(12) United States Patent
Harley et al.

(10) Patent No.: US 9,248,088 B2
(45) Date of Patent: Feb. 2, 2016

(54) COMPOSITIONS AND METHODS FOR SKIN CONDITIONING

(75) Inventors: Calvin B. Harley, Murphys, CA (US);
Allison C. Chin, Stanford, CA (US);
Tsutomu Akama, Sunnyvale, CA (US);
Nancy Yuk-yu Ip, Kowloon (HK);
Yung-hou Wong, Kowloon (HK); David M. Miller-Martini, Ridgway, PA (US)

(73) Assignee: TELOMERASE ACTIVATION SCIENCES, INC., New York, NY (US)

( * ) Notice: Subject to any disclaimer, the term of this patent is extended or adjusted under 35 U.S.C. 154(b) by 985 days.

(21) Appl. No.: 10/562,410

(22) PCT Filed: Jun. 24, 2004
(Under 37 CFR 1.47)

(86) PCT No.: PCT/US2004/020338
§ 371 (c)(1),
(2), (4) Date: Sep. 7, 2006

(87) PCT Pub. No.: WO2005/000248
PCT Pub. Date: Jan. 6, 2005

(65) Prior Publication Data
US 2007/0154435 A1 Jul. 5, 2007

Related U.S. Application Data

(60) Provisional application No. 60/482,630, filed on Jun. 25, 2003.

(51) Int. Cl.
*A61K 8/63* (2006.01)
*A61K 31/58* (2006.01)
(Continued)

(52) U.S. Cl.
CPC . *A61K 8/63* (2013.01); *A61K 31/56* (2013.01);
*A61K 31/58* (2013.01); *A61Q 19/00* (2013.01);
*A61Q 19/08* (2013.01); *A61Q 17/04* (2013.01)

(58) Field of Classification Search
CPC .......... A61K 8/63; A61K 31/58; A61K 31/56;
A61Q 19/08; A61Q 19/00; A61Q 17/04
See application file for complete search history.

(56) References Cited

U.S. PATENT DOCUMENTS

| 4,005,196 A | 1/1977 | Jandacek et al. |
| 4,509,949 A | 4/1985 | Huang et al. |

(Continued)

FOREIGN PATENT DOCUMENTS

| CN | 1283462 A | 2/2001 |
| CN | 1079265 C | 2/2002 |

(Continued)

OTHER PUBLICATIONS

Papadophoulos, George et al, Antioxidant Effect of Natural Phenols on Olive Oil, Sep. 1991, JAOCS, vol. 68, No. 9, 669-671.*

(Continued)

*Primary Examiner* — Trevor Love
(74) *Attorney, Agent, or Firm* — Wilmer Cutler Pickering Hale and Dorr LLP

(57) ABSTRACT

Methods and cosmetic compositions for conditioning the skin, utilizing as active ingredients selected compounds structurally related to astragenols, cycloastragenols, and/or protopanaxatriols, are provided. Such compounds include those of formulas (I), (II) and (III) described herein.

8 Claims, 8 Drawing Sheets

1 (Astragaloside IV)

2 (Cycloastragenol)

(51) Int. Cl.
*A61Q 19/08* (2006.01)
*A61Q 19/00* (2006.01)
*A61K 31/56* (2006.01)
*A61Q 17/04* (2006.01)

(56) References Cited

U.S. PATENT DOCUMENTS

| | | | |
|---|---|---|---|
| 4,518,772 A | 5/1985 | Volpenhein | |
| 4,599,379 A | 7/1986 | Flesher et al. | |
| 4,628,078 A | 12/1986 | Glover et al. | |
| 4,797,300 A | 1/1989 | Jandacek et al. | |
| 4,835,206 A | 5/1989 | Farrar et al. | |
| 4,849,484 A | 7/1989 | Heard | |
| 4,960,764 A | 10/1990 | Figueroa, Jr. et al. | |
| 5,011,681 A | 4/1991 | Ciotti et al. | |
| 5,069,897 A | 12/1991 | Orr | |
| 5,087,445 A | 2/1992 | Haffey et al. | |
| 5,100,660 A | 3/1992 | Hawe et al. | |
| 5,139,770 A | 8/1992 | Shih et al. | |
| 5,306,516 A | 4/1994 | Letton et al. | |
| 5,629,154 A | 5/1997 | Kim et al. | |
| 5,663,160 A | 9/1997 | Meybeck et al. | |
| 5,770,578 A | 6/1998 | Binder et al. | |
| 5,785,977 A | 7/1998 | Breithbarth | |
| 5,786,343 A | 7/1998 | Ber | |
| 5,891,639 A | 4/1999 | Harley et al. | |
| 5,916,565 A | 6/1999 | Rose et al. | |
| 5,942,233 A | 8/1999 | Chang | |
| 6,007,989 A | 12/1999 | West et al. | |
| 6,126,942 A | 10/2000 | Yang | |
| 6,153,208 A | 11/2000 | McAtee et al. | |
| 6,162,459 A | 12/2000 | Hu et al. | |
| 6,171,604 B1 * | 1/2001 | Mousa | 424/401 |
| 6,190,678 B1 | 2/2001 | Hasenoehrl et al. | |
| 6,277,396 B1 | 8/2001 | Dente | |
| 6,346,539 B1 | 2/2002 | Raman et al. | |
| 6,696,094 B2 * | 2/2004 | Wu | 424/725 |
| 6,855,344 B2 * | 2/2005 | Chou | 424/725 |
| 2002/0013260 A1 | 1/2002 | Jia | |
| 2002/0044977 A1 * | 4/2002 | Close | 424/725 |
| 2002/0164387 A1 * | 11/2002 | Wei et al. | 424/746 |
| 2002/0182272 A1 | 12/2002 | Halstead | |
| 2003/0108629 A1 * | 6/2003 | Chou | 424/765 |
| 2007/0122501 A1 | 5/2007 | Harley et al. | |
| 2008/0113925 A1 | 5/2008 | Harley et al. | |

FOREIGN PATENT DOCUMENTS

| | | |
|---|---|---|
| CN | 1383853 A | 12/2002 |
| CN | 1406585 A | 4/2003 |
| EP | 1295893 A1 | 3/2003 |
| EP | 1403252 | 3/2004 |
| JP | 62-12791 | 1/1987 |
| JP | 62-012791 | 1/1987 |
| JP | 8-503931 | 4/1996 |
| JP | 8-510474 | 11/1996 |
| JP | 10-36388 | 2/1998 |
| JP | 2000-204091 | 7/2000 |
| JP | 2000-229827 | 8/2000 |
| JP | 2000-229834 | 8/2000 |
| JP | 2003-089687 | 3/2003 |
| JP | 2003-160497 | 6/2003 |
| WO | WO 99/35243 A3 | 7/1999 |
| WO | WO 00/08135 A1 | 2/2000 |
| WO | WO 00/31238 A2 | 6/2000 |
| WO | WO 01/01996 A1 | 1/2001 |
| WO | WO-01/18015 A1 | 3/2001 |
| WO | WO-01/92289 A1 | 12/2001 |
| WO | WO-02/07732 | 1/2002 |
| WO | WO-02/69980 A2 | 9/2002 |
| WO | WO 02/091999 A2 | 11/2002 |
| WO | WO 02/091999 A3 | 11/2002 |
| WO | WO-2004/112724 | 12/2004 |
| WO | WO 2005/000245 A2 | 1/2005 |
| WO | WO 2005/044179 A2 | 5/2005 |

OTHER PUBLICATIONS

International Search report and Written Opinion for PCT application PCT/US04/20338, 7 pages, search report dated Apr. 12, 2005.
Funk, Walter D. et al., "Telomerase expression restores dermal integrity to in vitro-aged fibroblasts in a reconstituted skin model", *Experimental Cell Research*, 258(2):270-278 (2000).
Harle-Bachor, C. et al.,"Telomerase activity in the regenerative basal layer of the epidermis inhuman skin and in immortal and carcinoma-derived skin keratinocytes", *Proc Nat'l Acad. Sci. USA*, 93(13):6476-81 (1996).
Huang, Y. et al., "Selected non-timber forest products with medicinal applications from Jilin Province in China", Conference Title: Forest communities in the third millennium: Linking research, business, and policy toward a sustainable non-timber forest product sector; Kenora, Ontario, Canada, Oct. 1-4, 1999; General Technical Report—North Central Research Station, USDA Forest Service (No. NC-217): p. 93-101 (2000).
Kitagawa et al., Saponin and Sapogenol XXXIV. Chemical Constituents of Astragali Radix, the Root of Astragalus Membranaceus Bunge (1). Cycloastragenol, the 9,19-Cyclolanostane-type Aglycone of Astragalosides, and the Artifact Aglycone Astragenol, *Chem. Pharm. Bull.*, 31(2):689-697 (1983).
Kitagawa et al., Saponin and Sapogenol XXXV. Chemical Constituents of Astragali Radix, the Root of Astragalus Membranaceus Bunge (2). Astragalosides I, II and IV, Acetylastragaloside I and Isoastragalosides I and II, *Chem. Pharm. Bull.*, 31(2):698-708 (1983).
Pistelli, L., et al.,"Antimicrobial and antifungal activity of crude extracts and isolated saponins fromAstragalus verrucosus", *Fitoterapia*, 73(4):336-339 (2002).
Yasukawa et al., "Sterol and triterpene derivatives from plants inhibit the effects of a tumor promoter, and sitosterol and betulinic acid inhibit tumor formation in mouse skin two-stage carcinogenesis", *Oncology*, 48(1):72-76 (1991).
"Astragalus" www.drugs.com/npp/astragalus.html, 5 pages (Oct. 20, 2008).
Bedir, E. et al., "Cycloartane triterpene glycosides from the roots of *Astragalus brachypterus* and *Astragalus microcephalus*," *J. Nat. Prod.*, 61:1469-72 (1998).
Bedir, E. et al., "Immunostimulatory effects of cycloartane-type triterpene glycosides from *Astragalus* species", *Biol. Pharm. Bull.*, 23(7):834-837 (2000).
Bodnar, A. G. et al., "Extension of life-span by introduction of telomerase into normal human cells" *Science*, 279(5349):349-52 (1998).
Calzada, L. et al., "Effect of tetracyclic triterpenes (argentatins A, B and D) on the estradiol receptor of hormone-dependent tumors of human breast", *Medical Science Research*, 23(12):815-16 (1995).
Chiu, C. P. et al., "Replicative senescence and cell immortality: the role of telomeres and telomerase", *Proc. Soc. Exp. Biol. Med.*, 214(2):99-106 (Feb. 1997).
Chu, D-T. et al., "Fractionated extract of *Astragalus membranaceus*, a Chinese medicinal herb, potentiates lak cell cytotoxicity generated by a low dose of recombinant interleukin-2;" *J. Clin. Lab. Immunol.*, 26:183-7 (1988).
Chu, D-T. et al., "Immunotherapy with Chinese medicinal herbs. II Reversal of cyclophosphamide-induced immune suppression by administration of fractionated Astragalus membranaceus in vivo," *J. Clin. Lab. Immunol.*, 25:125-9 (1988).
Dagarag, M. et al., "Differential impairment of lytic and cytokine functions in senescent human immunodeficiency virus type 1-specific cytotox T lymphocytes", *Journal of Virology*, 77(5):3077-83 (2003).
Farwell, D. G. et al., "Genetic and epigenetic changes in human epithelial cells immortalized by telomerase", *American Journal of Pathology*, 156(5):1537-47 (2000).

(56) References Cited

OTHER PUBLICATIONS

Fujimoto, R. et al., "Expression of telomerase components in oral keratinocytes and squamous cell carcinomas", *Oral Oncology*, 37(2):132-40 (2001).
Harley, C. B. et al., "Telomeres shorten during ageing of human fibroblasts", *Nature*, 345(6274):458-60 (1990).
Henderson, S. et al., "In situ analysis of changes in telomere size during replicative aging and cell transformation", Journal of Cell Biology, 134(1):1-12 (1996).
Ionkova, I., "*Astragalus* species (Milk Vetch): in Vitro culture and the production of saponins, astragaline, and other biologically active compounds," Biotechnology in Agriculture and Forestry, vol. 33, *Medicinal and Aromatic Plants VIII*, Y. Bajaj, Ed., Springer Verlag, Berlin, pp. 97-138 (1995).
Kaneko, M. et al., "Accelerated recovery from cyclophosphamide-induced leukopenia in mice administered a Japanese ethical herbal drug, Hochu-ekki-to", *Immunopharmacology*, 44(3):223-231 (1999).
Kang, M. K. et al., "Replicative senescence of normal human oral keratinocytes is associated with the loss of telomerase activity without shortening of telomeres", *Cell Growth & Differentiation*, 9(1):85-95 (1998).
Khushbaktova, Z. A. et al.,"Influence of cycloartanes from plants of the genus *Astragalus* and their synthetic analogs on the contractive function of the rnyocarbium and the activity of Na, K-ATPase", *Chemistry of Natural Compounds*, 30(4):469-473 (1994).
Kinjo, J. et al., "Anti-herpes virus activity of fabaceous triterpenoidal saponins", *Biological & Pharmaceutical Bulletin* 23(7):887-9 (2000).
Lee, K. M. et al., "Immortalization with telomerase of the Nestin-positive cells of the human pancreas", *Biochem Biophys Res Commun*, 301(4):1038-44 (2003).
Juntao, L. et al., "Effect of retinoic acid and genseng on the telomerase activity in the liver cancer cell," *J. Trop. Med.*, 2(1):39-40 (2002) (English Abstract).
Mattson, M. P. ,"Emerging neuroprotective strategies for Alzheimer's disease: dietary restriction, telomerase activation, and stem cell therapy", *Experimental Gerontology*, 35(4):489-502 (2000).
Morales, C. P. et al., "Absence of cancer-associated changes in human fibroblasts immortalized with telomerase", *Nature Genetics*, 21(1):115-8 (1999).
Oda, K. et al., "Adjuvant and haemolytic activities of 47 saponins derived from medicinal and food plants", *Biological Chemistry*, 381(1):67-74 (2000).
Oh, H. and Schneider, M. D. ,"The emerging role of telomerase in cardiac muscle cell growth and survival", *Journal of Molecular Cellular Cardiology*, 34(7):717-24 (2002).
Simonsen, J. L. et al., "Telomerase expression extends the proliferative life-span and maintains the osteogenic potential of human bone marrow stromal cells", *Nature Biotechnology*, 20(6):592-6 (2002).
Thomas, M. , Yang, L. , and Hornsby, P. J., "Formation of functional tissue from transplanted adrenocortical cells expressing telomerase reverse transcriptase", *Nature Biotechnology*, 18(1):39-42 (2000).
Vasa, M. et al., "Nitric oxide activates telomerase and delays endothelial cell senescence", *Circulation Research*, 87(7):540-542 (2000).
Wang, Y-P. et al., "Effect of astragaloside IV on T, B lymphocyte proliferation and peritoneal macrophage function in mice", *Acta Pharmacologica Sinica*, 23(3): 263-6 (2002).
Xiao, H. et al., "Total analytical method for Radix astragali extract using two-binary multi-segment gradient elution liquid chromatography," *J. Sep. Sci.*, 24:186-96 (2001).
Yang, J. et al., "Telomerized human microvasculature is functional in vivo", *Nature Biotechnology*, 19(3):219-24 (2001).
Yang, J., et al., "Human endothelial cell life extension by telomerase expression", *The Journal of Biological Chemistry*, 274(37):26141-26148 (1999).
Yudoh, K. et al., "Reconstituting telomerase activity using the telomerase catalytic subunit prevents the telomere shorting and replicative senescence in human osteoblasts", *Journal of Bone and Mineral Research*, 16(8):1453-1464 (2001).
Zhang W. J. et al., "Regulation of the fibrinolytic potential of cultured human umbilical vein endothelial cells : astragaloside IV downregulates plasminogen activator inhibitor-1 and upregulates tissue-type plasminogen activator expression", *Journal of Vascular Research*, 34(4):273-80 (1997).
Zheng, Z. et al., "Studies on chemical constituents and immunological function activity of hairy root of Astragalus membranaceus," *Chinese Journal of Biotechnology*, 14(2):L93-7 (1998).
Zi-Pu, L. and Qian, C., "Effects of astragaloside IV on myocardial calcium transport and cardiac function in ischemic rats", *Acta Pharmacol Sin* 23(10):898-904 (2002).
Chen, J. & Chen, T., "Huang Qi (Radix Astragali)," *Chinese Medical Herbology and Pharmacology*, Chapter 17 Tonic Herbs, Art of Medicine Press, Inc., pp. 748-752 (2004).
Wang, D. et al., "Simultaneous analysis of seven astragalosides in Radix Astragali and related preparations by liquid chromatography coupled with electrospray ionization time-of-flight mass spectrometry," *J. Sep. Sci.* 29:2012-22 (2006).
Office Action dated Oct. 5, 2007 for U.S. Appl. No. 10/563,533.
Office Action dated Apr. 30, 2009 for U.S. Appl. No. 10/562,374.
Abdallah, R. et al., "Astragalosides from Egyptian astragalus spinosus vahl", *Die Pharmazie* 48(6) 1993 , pp. 452-454.
Fauce, S. et al., "Telomerase-based pharmacologic enhancement of antiviral function of human CD8+ T lymphocytes", *J. Immunol.* 181 2008 , pp. 7400-7406.
Ionkova, I. et al., "Cycloartane saponin production in hairy root cultures of Astragalus mongholicus", *Phytochemistry* 45(8) 1997 , pp. 1597-1600.
Li, C-X. et al., "Effects of Buyang Huanwu decoction and its active constituents on the fluidity of brain cell membrane in vitro", *Chinese Pharmaceutical Journal* 36(8) 2001 , pp. 528-531.
Luo, H. et al., "Nuclear cardiology study on effective ingredients of Astralagus membranaceus in treating heart failure", *Chin. J. Integrated Traditional and Western Med.* 15(12) 1995 , pp. 707-709.
Zhang, J. et al., "New drugs derived from medicinal plants", *Therapie* 57(2) 2002 , pp. 137-150.
Zhao, K. et al., "Enhancement of the immune response in mice by Astragalus membranaceus extracts", *Immunopharmacol.* 20 1990 , pp. 225-234.
Hasegawa, H. et al., "Inhibitory effect of some trierpenoid saponins on glucose transport in tumor cells and its application to in vitro cytotoxic and antiviral activities", *Planta Medica* 60(3) (1994) , pp. 240-243.
Kitagawa, I. et al., "Saponin and sapogenol. XXXVI. Chemical constituents of Astragali radix, the root of Astragalus membranaceous BUNGE. Astragalosides III, V, and VI", *Chem. Pharm. Bull.* 31(2) (1983) , pp. 709-715.
Pan, F. et al., "Studies on triterpenoids of *Astragalus floridus* ", *Acta Botanica Sinica* 38, (1996),pp. 836-838.
Carlotti et al., "Optimization of W/)-S Emulsions and Study of the Quantitative Relationships Between Ester Structure and Emulsion Properties," J. Dispersion Science and Technology, 13(3), pp. 315-336, 1992.
Choi, "Epidermis Proliferative Effect of the Panax Ginseng Ginsenoside Rb2," Arch. Pharm. Res., 2002, vol. 25, No. 1, pp. 71-76.
Dahms et al., "New Formulation Possibilities Offered by Silicone Copolyols," Cosmetics & Toiletries Magazine, vol. 110, Mar. 1995, pp. 91-100.
Franz et al., "Percutaneous Absorption of Fluocinonide in Man: Assessment of Relative Bioequivalence of 0.05% Lidex Ointment and Solution," The Journal of Investigative Dermatology, vol. 94, No. 4, Apr. 1990, pp. 525, 3 pages.
Smid-Korbar et al., "Efficiency and Usability of Silicone Surfactants in Emulsions," International Journal of Cosmetic Science 12, pp. 135-139, 1990.
Wang et al., "An Improved Oxidative Cleavage Method for Large Scale Preparation of Some Acid-labile Aglycones from Glycosides," Journal of the Chinese Chemical Society, 2002, vol. 49, No. 1, pp. 103-106.

(56) References Cited

OTHER PUBLICATIONS

Chen, et al., "Protective Effect of Ginsenoside Rg1 on Dopamine-Induced Apoptosis in PC12 Cells", Acta Pharmacol Sin, 22(8):673-678, Aug. 2001 (6 pages).

*CTFA International Cosmetic Ingredient Dictionary, Fourth Edition,* Nikitakis, et al., Editiors, The Cosmetic, Toiletry, and Fragrance Association, Washington, D.C., pp. 12 and 80, 1991 (5 pages).

De Navarre, *The Chemistry and Manufacture of Cosmetics, Second Edition, vol. I-IV,* Reprint by Continental Press, Orlando, Florida, 1975 (15 pages).

Franz, et al., "Percutaneous Absorption of Flucoinon in Man: Assessment of Relative Bioequivalence of 0.05% Lidex Ointment and Solution", Abstracts of the ESDR-JSID-SID Tricontinental Meeting, Washington, DC, May 2-5, 1990, Journal of Investigative Dermatology, 94(4):525, Apr. 1990 (2 pages).

Hameyer, "Comparative Technological Investigations of Organic and Organosilicone Emulsifiers in Cosmetic Water-in-Oil Emulsion Preparations," HAPPI, pp. 88, 90, 92, and 94, Apr. 1991 (4 pages).

*Harry's Cosmeticology, Seventh Edition,* Wilkinson, et al., Editors, George Godwin, London, 1982 (13 pages).

Hong, et al., "Stimulatory Effects of Ginsenoside-RG1 on p56lck Kinase and Cell Proliferation in Jurkat T Cells", Korean J. Ginseng Sci., 19(2):117-121, 1995 (6 pages).

Knowlton, et al., *Handbook of Cosmetic Science and Technology, 1st Edition,* Elsevier Advanced Technolgy, Oxford, United Kingdom, 1993 (4 pages).

Krzysik, et al., "A New Silicone Emulsifier for Water-in-Oil Systems", DCI: Drug & Cosmetic Industry, vol. 146, No. 4, pp. 28, 30, 35, 79, and 81, Apr. 1990 (7 pages).

Lee, et al., "Ginsenoside-Rg1, one of the major active molecules from Panax ginseng, is a functional ligand of glucocorticoid receptor", Molecular and Cellular Endocrinology, 133:135-140, 1997 (6 pages).

McCutchen's Emulsifiers & Detergents, North American Edition, McCutcheon Division, MC Publishing, Co., Glen Rock, NJ, 1986 (344 pages).

Pharmaceutical Dosage Forms: Disperse Systems, vol. 1, Lieberman, et al., Editors, Marcel Dekker, Inc., New York and Basel, 1988 (5 pages).

Pharmaceutical Dosage Forms: Disperse Systems, vol. 2, Lieberman, et al., Editors, Marcel Dekker, Inc., New York and Basel, 1989 (7 pages).

Yamamoto, et al., "The Accelerating Effects of Ginsenosides, Ginseng Saponins, on DNA Synthesis in Rat Bone Marrow Cells, in Comparison with some Cytokines and Growth Factors", J. Nissei Hosp, 24(1):12-13, 1996 (3 pages).

Yamamoto, et al., "The Stimulatory Effects of Ginseng Saponins on Proliferation and DNA Synthesis of Human Vascular Endothelial Cells and Skin Fibroblasts in Relation to Cytokines or Growth Factors", J. Nissei Hospital, 26(1):39-42, 1998 (4 pages).

\* cited by examiner

2 (Cycloastragenol)

4 (Astragaloside IV 16-one)

1 (Astragaloside IV)

3 (Astragenol)

6

8 (Ginsenoside RH1)

5

7

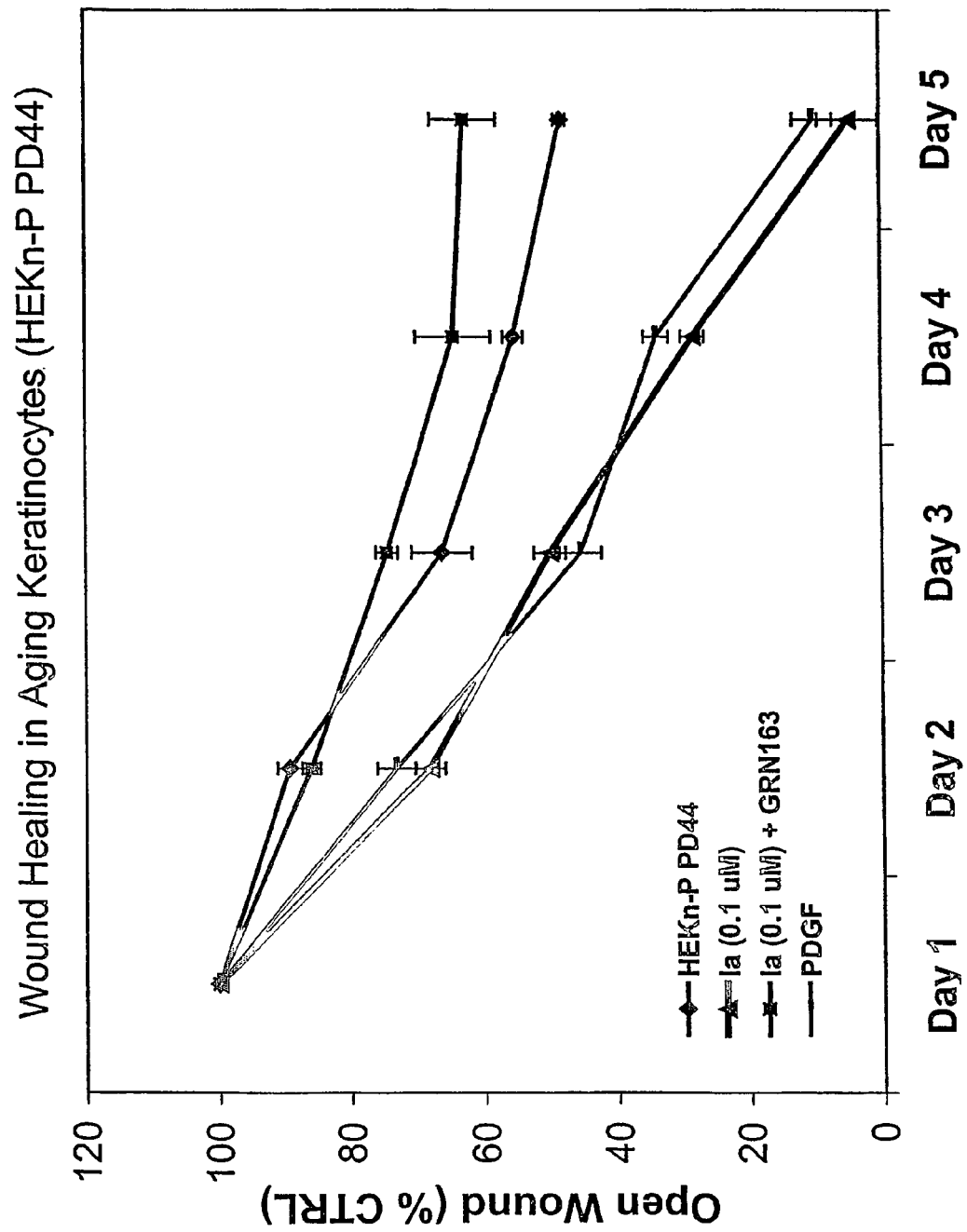

COMPOSITIONS AND METHODS FOR SKIN CONDITIONING

This application is a national stage filing of PCT Application No. PCT/US04/20338 filed Jun. 24, 2004, which claims priority to U.S. Provisional Application No. 60/482,630, filed Jun. 25, 2003, both of which are hereby incorporated by reference in their entirety.

FIELD OF THE INVENTION

The invention concerns methods and cosmetic compositions for conditioning the skin.

BACKGROUND OF THE INVENTION AND REFERENCES

Various compounds have been described in the art as active ingredients of cosmetic compositions for conditioning of the skin. These include, for example, vitamin B3 compounds such as niacinamide, natural and synthetic vitamin A derivatives, and estrogens and estrogen derivatives, as well as β-1,3-D-glucan (Ber, U.S. Pat. No. 5,786,343) and piperine derivatives (Raman et al., U.S. Pat. No. 6,346,539).

Compounds of the astragaloside and ginsenoside families have been reported as having various biological effects. References describing astragaloside and ginsenoside compounds and their uses include:

Bedir, E. et al., "Immunostimulatory effects of cycloartane-type triterpene glycosides from *Astragalus* species", *Biol & Pharm Bull* 23(7):834-7 (2000).

Binder, B. et al., "Use of triterpensaponins, such as notoginsenoside R1 (NR1) and/or astragaloside (ASIV) for preparing medicaments", U.S. Pat. No. 5,770,578 (June 1998).

Calzada, L. et al., "Effect of tetracyclic triterpenes (argentatins A, B and D) on the estradiol receptor of hormone-dependent tumors of human breast", *Medical Scienice Research* 23(12):815-16 (1995).

Chen, X. et al., "Protective effect of ginsenoside Rg1 on dopamin-induced apoptotis in PC12 cells", *Acta Pharmacol Sinica* 22(8):673-678 (2001).

Hashimoto, K. et al., "Skin tissue regeneration promoters comprising ginsenoside Rb1", WO 200192289 (2001); EP 1295893 A1 (2003).

Hong, H.-Y. et al., "Stimulatory effects of ginsenoside-Rg$_1$ on p56$^{lck}$ kinase and cell proliferation in Jurkat T cells", *Korean J. Ginseng Sci.* 19(2):117-21 (1995).

Huang, Y. et al., "Selected non-timber forest products with medicinal applications from Jilin Province in China", Conference Title: Forest communities in the third millennium: Linking research, business, and policy toward a sustainable non-timber forest product sector; Kenora, Ontario, Canada, 1-4 Oct., 1999; General Technical Report-North Central Research Station, USDA Forest Service (No. NC-217): p. 93-101 (2000).

Kaneko, M. et al., "Accelerated recovery from cyclophosphamide-induced leukopenia in mice administered a Japanese ethical herbal drug, Hochu-ekki-to", *Immunopharmacology* 44(3):223-231 (1999).

Kinjo, J. et al., "Anti-herpes virus activity of fabaceous triterpenoidal saponins", *Biological & Pharmaceutical Bulletin* 23(7):887-9 (July 2000).

Khushbaktova, Z. A. et al., "Influence of cycloartanes from plants of the genus *Astragalus* and their synthetic analogs on the contractive function of the myocardium and the activity of Na, K-ATPase", *Chem. Nat. Compounds* 30(4): 469-473 (1994).

Lee, Y. J. et al., "Ginsenoside-Rg1, one of the major active molecules from *Panax ginseng*, is a functional ligand of glucocorticoid receptor", *Mol Cell Endocrinol* 133(2):13540 (October 1997).

Oda, K. et al., "Adjuvant and haemolytic activities of 47 saponins derived from medicinal and food plants", *Biol. Chem.* 381(1):67-74 (2000).

Pistelli, L., et al., "Antimicrobial and antifungal activity of crude extracts and isolated saponins from *Astragalus verrucosus*", *Fitoterapia* 73(4): 336-339 (2002).

Prince, R. L. and Min, X., "Compositions and method for treating or preventing osteoporosis", PCT Pubn. No. WO 2001/01996.

Sengupta, S. et al., "Pharmaceutically effective compounds and their use", PCT Pubn. Nos. WO 2002/69980 and WO 2002/07732.

Wang, Y-P. et al., "Effect of astragaloside IV on T,B lymphocyte proliferation and peritoneal macrophage function in mice", *Acta Pharmacologica Sinica* 23(3):263-6 (March 2002).

Yasukawa, K. et al., "Sterol and triterpene derivatives from plants inhibit the effects of a tumor promoter, and sitosterol and betulinic acid inhibit tumor formation in mouse skin two-stage carcinogenesis", *Oncology* 48(1):72-6 (1991).

Yamamoto, M. et al., "The stimulatory effects of ginseng saponins on proliferation and DNA synthesis of human vascular endothelial cells and skin fibroblasts in relation to cytokines or growth factors", *Nissei Byoin Igaku Zasshi* 24(1):12-13 (1996).

Zhang W. J. et al., "Regulation of the fibrinolytic potential of cultured human umbilical vein endothelial cells: astragaloside IV downregulates plasminogen activator inhibitor-1 and upregulates tissue-type plasminogen activator expression", *Journal of Vascular Research* 34(4):273-80 (July-August 1997).

Zi-Pu, L. and Qian, C., "Effects of astragaloside IV on myocardial calcium transport and cardiac function in ischemic rats", *Acta Pharmacol Sin* 23(10): 898-904 (October 2002).

SUMMARY OF THE INVENTION

The present invention includes, in one aspect, a method for conditioning the skin, comprising applying topically to the skin a formulation comprising a compound of formula I, II or m below. In-formula I:

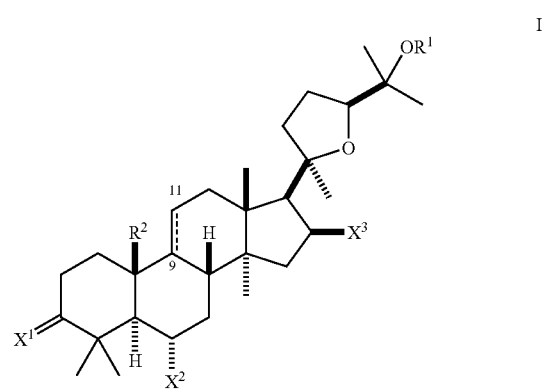

each of $X^1$, $X^2$, and $X^3$ is independently selected from hydroxy, lower alkoxy, lower acyloxy, keto, and a glycoside;

$OR^1$ is selected from hydroxy, lower alkoxy, lower acyloxy, and a glycoside;

wherein any of the hydroxyl groups on said glycoside may be substituted with a further glycoside, lower alkyl, or lower acyl, such that the compound includes a maximum of three glycosides; and $R^2$ is methyl and === represents a double bond between carbons 9 and 11; or, in preferred embodiments, $R^2$ forms, together with carbon 9, a fused cyclopropyl ring, and === represents a single bond between carbons 9 and 11.

Preferably, the compound includes zero, one, or two, more preferably zero or two, glycosides, none of which is substituted with a further glycoside. Preferably, glycosides are of the D (naturally occurring) configuration.

In selected embodiments of formula I, each of $X^1$ and $X^2$ is independently selected from hydroxy, lower alkoxy, lower acyloxy, and a glycoside, and $X^3$ is selected from hydroxy, lower alkoxy, lower acyloxy, keto, and a glycoside. In further embodiments, $X^1$ is OH or a glycoside, each of $X^2$ and $OR^1$ is independently OH or a glycoside, and $X^3$ is OH or keto. Exemplary compounds of formula I include astragaloside IV, cycloastragenol, astragenol, astragaloside IV 16-one, cycloastragenol 6-β-D-glucopyranoside, and cycloastragenol 3-β-D-xylopyranoside. In selected embodiments, the compound is selected from astragaloside IV, cycloastragenol, astragenol, and astragaloside IV 16-one. In one embodiment, the compound is astragaloside IV.

In compounds of formula II:

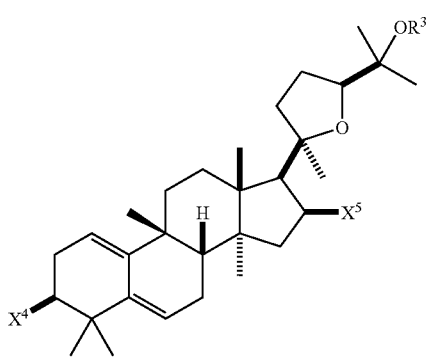

each of $X^4$ and $X^5$ is independently selected from hydroxy, lower alkoxy, lower acyloxy, keto, and a glycoside, and $OR^3$ is selected from hydroxy, lower alkoxy, lower acyloxy, and a glycoside, wherein any of the hydroxyl groups on said glycoside may be substituted with a further glycoside, lower alkyl, or lower acyl, such that the compound includes a maximum of three glycosides.

Preferably, the compound includes zero, one, or two glycosides, none of which is substituted with a further glycoside; glycosides are preferably of the D configuration.

In selected embodiments of formula II, each of $X^4$ and $OR^3$ is selected from hydroxy, lower alkoxy, lower acyloxy, and a glycoside, and $X^5$ is selected from hydroxy, lower alkoxy, lower acyloxy, and keto (=O). In further embodiments, $X^4$ is OH or a glycoside, and each of $X^5$ and $OR^3$ is OH. In one embodiment, $X^4$ is OH.

In compounds of formula III:

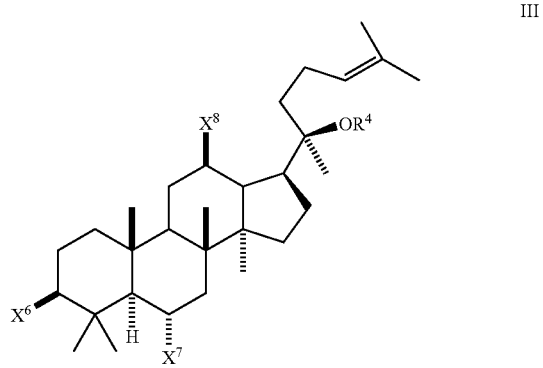

each of $X^6$, $X^7$, and $X^8$ is independently selected from hydroxy, lower alkoxy, lower acyloxy, keto, and a glycoside, and $OR^4$ is selected from hydroxy, lower alkoxy, lower acyloxy, and a glycoside, wherein any of the hydroxyl groups on said glycoside may be substituted with a further glycoside, lower alkyl, or lower acyl, such that the compound includes a maximum of three glycosides.

Preferably, the compound includes zero, one, or two glycosides, none of which is substituted with a further glycoside; glycosides are preferably of the D configuration.

In selected embodiments of formula E, each of $X^6$, $X^7$, $X^8$ and $OR^4$ is independently selected from hydroxy, lower alkoxy, lower acyloxy, and a glycoside, and is preferably selected from hydroxy and a glycoside. In further embodiments, each of $X^8$ and $OR^4$ is OH, and each of $X^6$ and $X^7$ is independently selected from hydroxyl and a glycoside. In still further embodiments, each of $OR^4$, $X^6$ and $X^8$ is OH, and $X^7$ is a glycoside. An exemplary compound of formula III is ginsenoside RH1.

Preferably, the compound selected from the group consisting of formulas I-III above is present in a cosmetic formulation, which forms a further aspect of the invention, at a concentration of 0.01% (w/v) or greater. Preferred embodiments of the compounds include those described above. In selected embodiments, the compound is selected from astragaloside IV, cycloastragenol, astragenol, astragaloside IV 16-one, cycloastragenol 6-β-D-glucopyranoside, cycloastragenol 3-β-D-xylopyranoside, and 20R,24S-epoxy-3β,16β,25-trihydroxy-9β-methyl-19-norlanost-1,5-diene (designated herein as 5).

The cosmetic vehicle in the formulations of the invention typically comprises one or more ingredients conventional to cosmetic formulations, as described further below, such as an emulsifier, a thickener, and/or a skin emollient. In selected embodiments, the formulation comprises an emulsifier and/or a skin emollient; in further embodiments, the formulation comprises at least a skin emollient. In each case, the emulsifier, thickener, and/or skin emollient is one that is conventionally used in cosmetic formulations, as described further below.

In selected embodiments, the formulation contains from 0.01% to 10% (w/v) of one or more compounds of structure I, II or III. In other selected embodiments, the formulation contains about 0.01 to 1%, or about 0.05 to 5% (w/v) of such a compound or combination of compounds. In one embodiment, the formulation contains at least 0.005% (w/v) but less than 0.1% (w/v) of such a compound or combination of compounds, e.g., the compound designated herein as 1 or 2, or a combination thereof. The formulation may also contain other ingredients conventional to cosmetic formulations, as described further below.

A preferred compound of formula I, II or III above, when formulated in a solvent at a concentration of 1 µg/ml or less, is effective to produce a level of telomerase activity in keratinocytes or fibroblasts, as measured in a TRAP assay, at least 25% greater than the level in said cells treated with said solvent, as measured in a TRAP assay as described herein. In further preferred embodiments, the compound is effective to produce a level of telomerase activity in keratinocytes or fibroblasts, as measured in a TRAP assay, at least 50% greater than the level in said cells treated with said solvent, as measured in a TRAP assay as described herein. In another preferred embodiment, the biological activity of the compound of formula I, II or III is such that the compound is effective, at a concentration of 1 µg/ml or less, to produce an amount of cell reconfluence in keratinocytes or fibroblasts, as measured in a scratch assay as described herein, which is at least 25% greater, preferably at least 50% greater, than that measured in untreated or other control cells.

These and other objects and features of the invention will become more fully apparent when the following detailed description of the invention is read in conjunction with the accompanying drawings.

BRIEF DESCRIPTION OF THE DRAWINGS

FIG. 7 is a graph showing activity of 1 (astragaloside IV) in a scratch assay of aging neonatal keratinocytes, in the presence and absence of the telomerase inhibitor GRN163, and in comparison with ~2 nM PDGF (platelet derived growth factor).

DETAILED DESCRIPTION OF THE INVENTION

I. Definitions

Figure 1B:
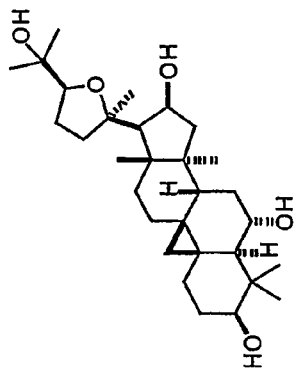
FIGS. 1A-H show the structures of exemplary compounds of formulas I-III as described herein.
Figure 1D:
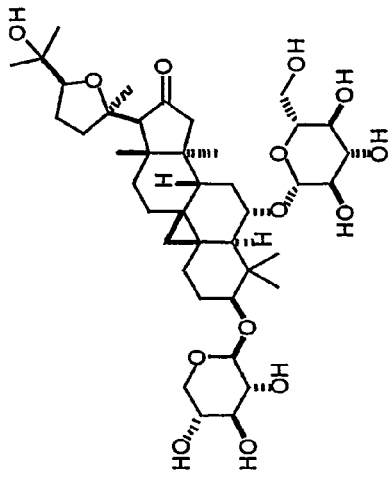
Figure 1A:
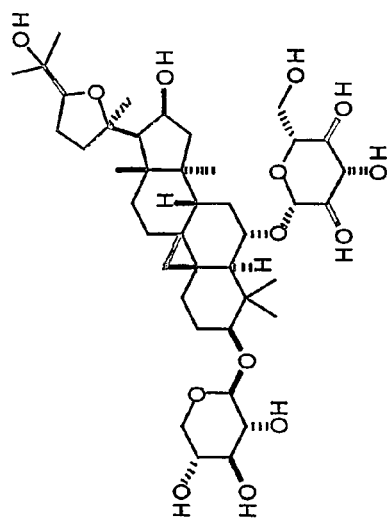
Figure 1C:
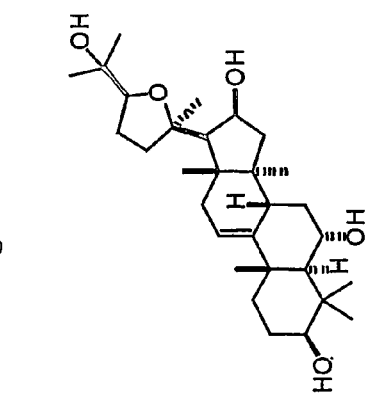
Figure 1F:
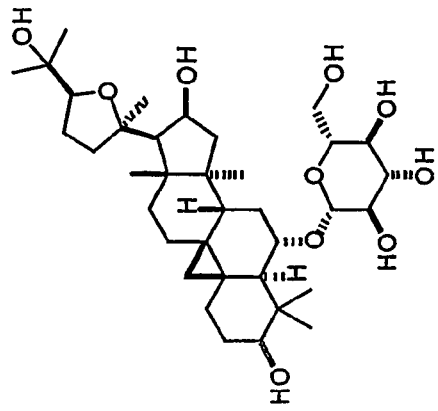
Figure 1H:
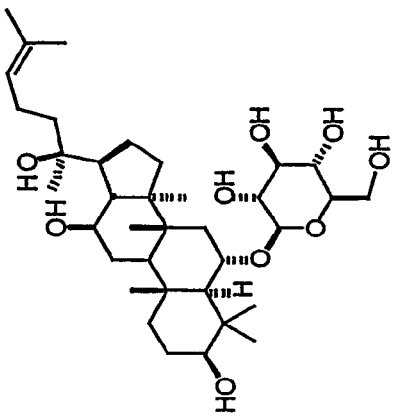
Figure 1E:
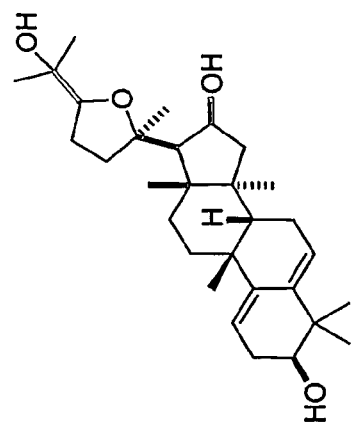
Figure 1G:
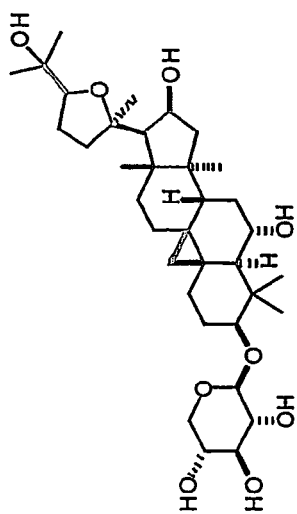

The following terms, as used herein, have the meanings given below, unless indicated otherwise.

"Conditioning the skin" includes such effects as improving the appearance, elasticity, thickness, or smoothness of skin, protecting skin from UV radiation, and/or reducing signs of skin aging, such as excessive dryness or wrinkling. Such signs of aging may be macroscopic, i.e. visually or tactilely apparent skin features, or they may be on a more microscopic or cellular level, such as cellular senescence of skin cells.

A "cosmetic vehicle" or "cosmetically acceptable vehicle" refers to a vehicle formulated for application to the skin, e.g. as a cream, gel, lotion, or ointment, and containing one or more components selected from emulsifiers, surfactants, thickeners, emollients, and lubricants. Such a vehicle is not intended or suitable for internal consumption.

A "safe and effective amount" refers to an amount sufficient to induce a significant benefit, but to minimize undesired side effects; i.e. to provide a reasonable risk to benefit ratio.

A general carbon atom numbering scheme used for nomenclature of compounds described herein is shown below. (Note that compounds of structure II lack the 19 carbon, and compounds of structure III lack the 18 carbon shown in this scheme. Accordingly, the numbering scheme is not intended to limit the methods or compositions described herein.)

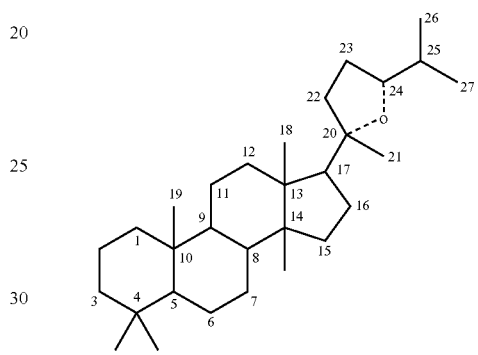

"Alkyl" refers to a fully saturated acyclic monovalent radical containing carbon and hydrogen, which may be branched or linear. Examples of alkyl groups are methyl, ethyl, n-butyl, t-butyl, n-heptyl, and isopropyl. "Alkoxy" refers to a group of the form OR, where R is alkyl as defined above. "Acyloxy" refers to a group of the form —OC(=O)R, where R is alkyl as defined above. Accordingly, "acyl" refers to the group —C(=O)R.

"Lower alkyl" (or lower alkoxy, or lower acyloxy) refers to such a group having one to six carbon atoms; in selected embodiments, such groups include one to four carbon atoms, one or two carbon atoms, or one carbon atom (i.e. methyl, methoxy, acetyloxy).

In concentrations expressed herein as % (w/v), 100% (w/v) corresponds to 1 g solute/ml solvent. For example, 0.1% (w/v)=1 mg/ml.

II. Cosmetic Compositions and Methods

In one aspect, the invention provides a method for conditioning the skin, regulating signs of skin aging, and/or protecting the skin from UV radiation. In accordance with the method, a formulation comprising, as an active ingredient, a compound of structure I, II, or III as described below, preferably a compound of structure I or II, in a cosmetic vehicle, as defined further below, is applied topically to the skin. As demonstrated below, the compounds are effective to increase telomerase activity and to promote cell proliferation in the skin. Benefits of such activity are manifested in suppression of signs of aging in the skin.

Preferably, the formulations used in the methods and compositions of the invention are formulations of an isolated compound of structure I, II, or III, preferably an isolated compound of structure I or II. As used herein, a "formulation of an isolated compound" refers to a formulation prepared by combining the isolated compound with one or more other ingredients (which may be active or inactive ingredients) to produce the formulation. Where the compound has been directly purified from a natural source, the phrase "isolated compound" requires that the compound (prior to the formulation) has been purified not less than 100-fold compared to the purity of the compound in the natural source. Where the compound is not purified directly from a natural source, the phrase "isolated compound" refers to a compound that (prior to the formulation) has been produced by a process involving one or more chemical synthesis steps, resulting in a preparation of the compound that is of not less than 5% (w/w) purity.

The cosmetic formulation may contain varying amounts of a compound or compounds of structure I, II, or III, generally at a level of at least 0.01% (w/v), up to about 5% (w/v). More typically, the formulation contains about 0.1 to 1% (w/v) of a compound of structure I, II, or III. In one embodiment, the formulation contains less than 0.1% (w/v) of such a compound or combination of compounds. The formulation also contains other ingredients conventional to cosmetic formulations, as described further below.

A. Cosmetic Vehicle

A1. Product Forms

The subject compositions may include a wide variety of product forms, including, for example, lotions, creams, gels, ointments, sticks, sprays, or pastes. These product forms may comprise several types of carriers, including, but not limited to, solutions, aerosols, emulsions, gels, solids, and liposomes. The carrier is frequently formulated as an emulsion, as described further below.

When the composition is formulated as an ointment, it may comprise a simple carrier base of animal or vegetable oils or semi-solid hydrocarbons, or an absorption ointment base which absorbs water to form an emulsion. Aerosols can be formed by adding a propellant, such as halogenated hydrocarbons known in the art, to a solution of the subject compound in a carrier such as described above. Aerosols are typically applied to the skin as a spray-on product.

The compositions of the present invention comprise a dermatologically acceptable carrier, within which the active ingredient and other components are incorporated, to allow these components to be delivered to the skin at an appropriate concentration. The carrier may contain one or more dermatologically acceptable solid, semi-solid or liquid fillers, diluents, solvents, extenders and the like. The carrier may be solid, semi-solid or liquid; preferred carriers are substantially liquid. The carrier should be physically and chemically compatible with the active ingredient and other components described herein. Preferred carriers contain a dermatologically acceptable, hydrophilic diluent; e.g., water, lower monovalent alcohols, low molecular weight glycols and polyols, such as propylene glycol, polyethylene glycol, polypropylene glycol, glycerol, butylene glycol, 1,2,4-butanetriol, sorbitol esters, 1,2,6-hexanetriol, and butanediol, ethoxylated ethers, propoxylated ethers, and combinations thereof. Water is a preferred diluent. The composition preferably comprises from about 60% to about 99% of the hydrophilic diluent.

In one embodiment, the formulation comprises an emulsion containing a hydrophilic phase, e.g., water or other hydrophilic diluent, and a hydrophobic phase, e.g., a lipid, oil or oily material, where one phase is dispersed in the other, continuous, phase. Examples are oil-in-water emulsions, water in oil emulsions, and water-in-silicone emulsions. Generally, the emulsion contains about 1% to 98% of the hydrophilic phase and about 1% to 50% of the hydrophobic phase. The emulsion may also comprise a gel network or a multiphase emulsion.

Preferred emulsions have an apparent viscosity at room temperature of from about 5,000 to about 200,000 centipoise (cps), depending on the physical form of the formulation. For example, a lotion may have an apparent viscosity of from about 10,000 to about 40,000 cps, and a cream may have an apparent viscosity of from about 60,000 to about 160,000 cps.

Suitable hydrophobic components employed in emulsions include, for example, vegetable oils, e.g. safflower oil, coconut oil, cottonseed oil, palm oil, soybean oil, and the like, which may be hydrogenated; animal fats and oils, such as lanolin; mineral oil; petrolatum, or petroleum jelly; or C7 to C40 hydrocarbons, e.g. such as dodecane, squalane, cholestanes, hydrogenated polyisobutylene, docosane, and various isoparaffins (branched hydrocarbons). Also suitable are esters of C1-C30 carboxylic acids and of C2-C30 dicarboxylic acids, where the alcohol component is derived from C1-C30 alcohols, glycols, or glycerols. Examples include, but are by no means limited to, isopropyl myristate, methyl palmitate, myristyl propionate, cetyl palmitate, dioctyl maleate, dioctyl sebacate, caprylic/capric triglyceride, PEG-8 caprylic/capric triglyceride, and ethylene glycol distearate; as well as propoxylated and ethoxylated derivatives thereof.

C1-C30 mono- and polyesters of sugars or other polyol moieties may also be used, as is known in the art, and include, for example, liquid materials such as glucose tetraoleate, glucose and mannose tetraesters of soybean oil fatty acids, galactose tetraesters of oleic acid, sorbitol hexaesters of unsaturated soybean oil fatty acids, and sucrose octaoleate. Solid materials include, for example, a sucrose polyester in which the degree of esterification is 7-8, and in which the fatty acid moieties are C18 mono- and/or di-unsaturated and behenic. Esters suitable for use in cosmetic emulsions are further described in, for example, U.S. Pat. Nos. 4,005,196, 5,306,516, 4,797,300, and 4,518,772. Also useful are C4-C20 alkyl ethers of polypropylene glycols, e.g. PPG-14 butyl ether, PPG-15 stearyl ether, dioctyl ether, dodecyl octyl ether, and mixtures thereof.

The hydrophobic component employed in an emulsion may also be an organopolysiloxane oil, such as disclosed in U.S. Pat. No. 5,069,897 (Orr). Examples of suitable organopolysiloxane oils include polyalkylsiloxanes, cyclic polyalkylsiloxanes, and polyalkylarylsiloxanes. Commercially available polyalkylsiloxanes include the polydimethylsiloxanes, which are also known as dimethicones, examples of which include the Vicasil™ series (General Electric) and the Dow Corning™ 200 series. Examples of alkyl-substituted dimethicones include cetyl dimethicone and lauryl dimethicone. Commercially available cyclic polyalkylsiloxanes include the cyclomethicones. Also useful are materials such as trimethylsiloxysilicate, such as that sold as a mixture with dimethicone as Dow Corning™ 593 fluid, and polyalkylaryl siloxanes.

A2. Components

Formulations of the present invention, particularly emulsions, preferably include one or more components selected from emulsifiers, surfactants, structuring agents, thickeners, and emollients, as described below., A2(a). Emulsifiers and Surfactants An emulsifier and/or surfactant is employed to disperse and suspend the discontinuous phase within the continuous phase. The surfactant should be hydrophilic enough to disperse in the hydrophilic phase; preferred surfactants are those having an HLB of at least about 8. The choice of surfactant will also depend upon the pH of the composition and the other components present.

Preferred hydrophilic surfactants are selected from nonionic surfactants, including those broadly defined as condensation products of long chain alcohols, e.g. C8-30 alcohols, with sugar or starch polymers, i.e., glycosides. Commercially available examples include decyl polyglucoside (available as APG 325 CS from Henkel) and lauryl polyglucoside (available as APG 600 CS and 625 CS from Henkel). Other useful nonionic surfactants include alkylene oxide esters and diesters of fatty acids, and alkylene oxide ethers of fatty alcohols, as well as the condensation products of alkylene oxides with both fatty acids and fatty alcohols. Nonlimiting examples of alkylene oxide-derived nonionic surfactants include ceteth-12, ceteareth-10, steareth-12, PEG-10 stearate, PEG-100 stearate, PEG-20 glyceryl stearate, PEG-80 glyceryl tallowate, PEG-30 glyceryl cocoate, PEG-200 glyceryl tallowate, PEG-8 dilaurate, PEG-10 distearate, and mixtures thereof. Still other useful nonionic surfactants include polyhydroxy fatty acid amides, such as coconut alkyl N-methyl glucoside amide.

The hydrophilic surfactants useful herein can also include any of a wide variety of cationic, anionic, zwitterionic, and amphoteric surfactants such as are known in the art. See, e.g., McCutcheon's, Detergents and Emulsifiers, North American Edition (1986), published by Allured Publishing Corporation; or U.S. Pat. No. 5,011,681 (Ciotti et al.). Cationic surfactants include, for example, cationic ammonium salts, such as quaternary ammonium salts, and amino-amides. Anionic surfactants include the alkyl isethionates (e.g., C12-C30), alkyl and alkyl ether sulfates and phosphates, alkyl methyl taurates, and alkali metal salts of fatty acids. Examples of amphoteric and zwitterionic surfactants include derivatives of aliphatic secondary and tertiary amines in which one aliphatic substituent contains from about 8 to about 22 carbon atoms and one contains an anionic water solubilizing group, e.g., carboxy, sulfonate, sulfate, phosphate, or phosphonate. Examples are alkyl imino acetates, iminodialkanoates and aminoalkanoates, imidazolinium and ammonium derivatives. Other suitable amphoteric and zwitterionic surfactants include betaines, sultaines, hydroxysultaines, alkyl sarcosinates (e.g., C12-C30), and alkanoyl sarcosinates.

Silicone containing emulsifiers or surfactants include dimethicone copolyols, i.e. polydimethyl siloxanes having polyether side chains, as well as dimethicone copolyols modified with pendant alkyl, cationic, anionic, amphoteric, and zwitterionic moieties. Dimethicone copolyol emulsifiers useful herein are described, for example, in U.S. Pat. No. 4,960,764 (Figueroa, Jr. et al.); G. H. Dahms et al., Cosmetics & Toiletries, vol. 110, pp. 91-100, 1995; M. E. Carlotti et al., J. Dispersion Science & Technology, 13(3), 315-336 (1992); P. Hameyer, HAPPI 28(4), pp. 88-128 (1991); J. Smid-Korbar et al., Intl Journal of Cosmetic Science, 12, 135-139 (1990); and D. G. Krzysik et al., Drug and Cosmetic Industry, vol. 146(4) pp. 28-81 (1990).

A2(b). Structuring Agents

The subject formulations, particular when in the form of an oil-in-water emulsion, may contain a structuring agent, preferably at a level of about 2% to about 9%. Preferred structuring agents are those having an HLB (hydrophile-lipophile balance) of about 1-8 and a melting point of at least about 45° C. Suitable structuring agents include, for example, saturated C14 to C30 fatty alcohols or amines, which may contain 1 to about 5 moles of ethylene oxide; saturated C16 to C30 diols; saturated C16 to C30 monoglycerol ethers; C14 to C30 saturated fatty acids, which may be hydroxylated or ethoxylated; C14 to C30 saturated glyceryl monoesters having a monoglyceride content of about 40% or more; C14 to C30 saturated polyglycerol esters having from about 1 to about 3 alkyl groups and from about 2 to about 3 saturated glycerol units; C14 to C30 glyceryl monoethers; C14 to C30 sorbitan mono/diesters or saturated methyl glucoside esters, which may be ethoxylated and/or contain 1 to about 5 moles of ethylene oxide; C14 to C30 saturated sucrose mono/diesters; C14 to C30 saturated polyglucosides having an average of 1 to 2 glucose units, and mixtures thereof. In selected embodiments, the structuring agent includes stearyl alcohol, cetyl alcohol, behenyl alcohol, a polyethylene glycol ether of stearyl or cetyl alcohol having an average of about 2 ethylene oxide units, and mixtures thereof A2(c). Thickeners and Gelling Agents The compositions of the present invention can also comprise a thickening or gelling agent, preferably in a level of about 0.1% to about 5%, more preferably from about 0.1% to about 3%, and most preferably from about 0.25% to about 2%. Nonlimiting classes of thickening agents include, for example, crosslinked polymers of acrylic acid, substituted acrylic acids, such as methacrylic acid, and salts and esters thereof, where the crosslinking agent is typically derived from a polyhydric alcohol. Preferred crosslinkers include allyl ethers of sucrose or of pentaerythritol. Also included are copolymers with acrylate esters, e.g. one short chain (C1-C4) and one long chain (C8-C40) acrylate ester. See, for example, U.S. Pat. No. 5,087,445 (Haffey et al.) or U.S. Pat. No. 4,509,949 (Huang et al.), as well as the CTFA International Cosmetic Ingredient Dictionary, fourth edition, 1991, pp. 12 and 80. Commercially available polymers of this type include the carbomers, which are homopolymers of acrylic acid crosslinked with allyl ethers of sucrose or pentaerytritol, e.g. the Carbopol™ 900 series (B.F. Goodrich), and acrylates/C10-30 alkyl acrylate crosspolymers, e.g. Carbopol™ 1342 and 1382 (B.F. Goodrich).

Crosslinked polyacrylate polymers are also used as thickeners or gelling agents, and include both cationic and nonionic polymers, with the cationic polymers being generally preferred. See, for example, U.S. Pat. No. 5,100,660 (Hawe et al.), U.S. Pat. No. 4,849,484 (Heard) U.S. Pat. No. 4,835,206 (Farrar et al.) U.S. Pat. No. 4,628,078 (Glover et al.), and U.S. Pat. No. 4,599,379 (Flesher et al.). In general, these materials are high molecular weight copolymers of a dialkylaminoalkyl acrylate monomer and a dialkylaminoalkyl methacrylate monomer, or their quaternary ammonium or acid addition salts, and may also incorporate any of a variety of unsaturated third monomers, such as ethylene, propylene, butylene, isobutylene, eicosene, maleic anhydride, acrylamide, methacrylamide, maleic acid, acrolein, cyclohexene, ethyl vinyl ether, and methyl vinyl ether. The alkyl portions of the acrylate monomers are preferably short chain alkyls such as C1-C8. Crosslinking agents, generally included to increase the viscosifying effect of the polymer, include methylenebisacrylamides, diallyldialkyl ammonium halides, polyalkenyl polyethers of polyhydric alcohols, allyl acrylates, vinyloxyalkylacrylates, and polyfunctional vinylidenes. Examples of such cationic polymers include Salcare™ SC92 and SC95 (Allied Colloids Ltd., Norfolk Va.), both provided as mineral oil dispersions.

Also useful as thickeners are polymers such as high molecular weight polyacrylamides, including block copolymers of acrylamides and substituted acrylamides with acrylic acids and substituted acrylic acids, e.g. Hypan™ SR150H, SS500V, SS500W, and SSSA100H (Lipo Chemicals, Inc., Patterson, N.J.); polysaccharides, e.g. cellulose, carboxymethyl hydroxyethylcellulose, hydroxypropylcellulose, sodium cellulose sulfate, and the like, as well as alkyl substituted celluloses, such as cetyl hydroxyethylcellulose; crosslinked vinyl ether/maleic anhydride copolymers; and crosslinked poly(N-vinylpyrrolidones), as described, for example, in U.S. Pat. No. 5,139,770 (Shih et al.). Commercially available examples include ACP-1120, -1179, and -1180 (International Specialty Products, Wayne, N.J.).

Thickening and gelling agents may also include materials derived from natural sources, such as acacia, agar, algin, amylopectin, carrageenan, carnitine, dextrin, gelatin, gellan gum, guar gum, hectorite, hyaluroinic acid, hydrated silica, chitosan, kelp, locust bean gum, natto gum, tragacanth gum, xanthan gum, derivatives thereof, and mixtures thereof.

A2(d). Emollients

The subject formulations may also include a dermatologically acceptable emollient, e.g. at a level of about 2% to about 50%, depending on the physical form of the formulation. For example, lotions typically comprise about 5% to 10% emollient and about 60% to 80% water. A cream typically comprises about 10% to 20% emollient and about 50% to 75% water. An ointment may comprise about 2% to 10% emollient and about 0.1% to 2% of a thickening agent as described below. Generally, the emollient is present at a level of about 5% to about 25%.

Emollients are typically water-immiscible, oily or waxy materials which serve to lubricate the skin. An emollient may be selected from one or more of the following classes: triglyceride esters, which include, for example, vegetable and animal fats and oils; acetylated or ethoxylated glycerides; alkyl or alkyenyl esters of fatty acids, e.g. methyl palmitate, isopropyl isostearate, diisohexyl adipate, cetyl lactate, oleyl stearate, and the like; long chain fatty acids or alcohols such as myristic, palmitic, stearic, oleic, behenic, hydroxystearyl, and the like; lanolin and lanolin derivatives; polyhydric alcohol esters, e.g. mono and di-fatty acid esters of ethylene glycol, diethylene glycol, polyethylene glycol (200-6000), propylene glycol, and polypropylene glycol, and sorbitan, which may be ethoxylated; wax esters such as beeswax, spermaceti, and ethoxylated derivatives thereof; vegetable waxes such as carnauba and candelilla waxes; phospholipids such as lecithin and derivatives thereof, sterols, such as cholesterol and its fatty acid esters; and fatty acid amides.

Additional types of conditioning compounds include polyhydric alcohols and their derivatives, such as, for example, polypropylene glycol, hydroxypropyl sorbitol, pentaerythritol, xylitol, ethoxylated glycerol, soluble collagen, dibutyl phthalate, or gelatin. Also useful are ammonium and quaternary alkyl ammonium glycolates and lactates; aloe vera gel; and hyaluronic acid and derivatives thereof A2(e). Other Components The formulations of the present invention may comprise a wide variety of additional components, as known in the art, including but not limited to anticaking agents, antimicrobial agents, astringents, opacifying agents, fragrances, pigments, preservatives, propellants, reducing agents, skin penetration enhancing agents, waxes, sunscreens, antioxidants and/or radical scavengers, chelating agents, sequestrants, anti-inflammatory agents, and vitamins. See, for example, Harry's Cosmeticology, 7th Ed., Harry & Wilkinson (Hill Publishers, London 1982); Pharmaceutical Dosage Forms-Disperse Systems; Lieberman, Rieger & Banker, Vols. 1 (1988) & 2 (1989); Marcel Decker, Inc.; The Chemistry and Manufacture of Cosmetics, 2nd. Ed., deNavarre (Van Nostrand 1962-1965); and The Handbook of Cosmetic Science and Technology, 1 st Ed. Knowlton & Pearce (Elsevier 1993).

Such additional components should be physically and chemically compatible with the vehicle and active components described herein, and not unduly impair stability, efficacy or other use benefits associated with the compositions of the present invention.

The compositions of the present invention are preferably formulated to have a pH of 10.5 or below, more preferably from about 3-8, and most more preferably from about 5-8.

B. Subject Compounds

In accordance with the present invention, compounds represented by formula I-III herein are useful in methods of conditioning the skin. In one embodiment, the compounds are represented by formula I:

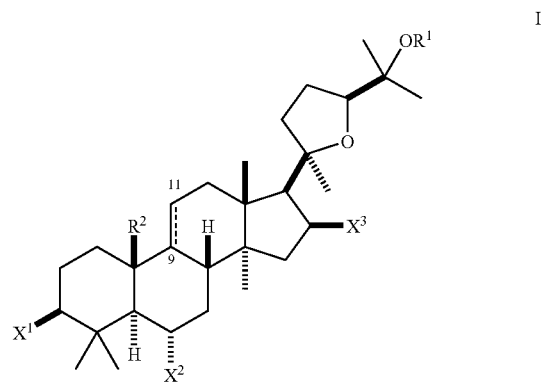

In formula I, each of $X^1$, $X^2$, and $X^3$ is independently selected from hydroxy, lower alkoxy, lower acyloxy, keto, and a glycoside, and the group $OR^1$ is selected from hydroxy, lower alkoxy, lower acyloxy, and a glycoside. In selected embodiments, each of $X^1$ and $X^2$ is independently selected from hydroxy, lower alkoxy, lower acyloxy, and a glycoside.

In selected embodiments of formula I, $R^2$ is methyl and ==== represents a double bond between carbons 9 and 11, as depicted. In other embodiments, $R^2$ forms, together with carbon 9, a fused cyclopropyl ring; and ==== represents a single bond between carbons 9 and 11, as shown for example, in compound 1 (see FIG. 1).

By a "glycoside", as used herein in reference to any of the subject compounds of formulas I, II, or m, is meant one of the known glycosides (i.e. riboside, arabinoside, xyloside, lyxoside, altroside, glucoside, mannoside, guloside, idoside, galactoside, and taloside). The glycoside is typically in the six-membered ring (pyranose) form, e.g., glucopyranoside or mannopyranoside. In selected embodiments, the glycoside is a D-glycoside; that is, it has the configuration found in naturally occurring monosaccharides. Specific examples include D-ribopyranoside, D-arabinopyranoside, D-xylopyranoside, D-glucopyranoside, mannopyranoside, and D-galactopyranoside. Preferred glycosides include D-glucopyranoside and D-xylopyranoside. In further embodiments, the linkage is of the β configuration; e.g. β-D-glucopyranoside.

Any of the free hydroxyl groups on a glycoside ring present in the subject compounds of formulas I, II, or III (or derivatives thereof) may be further substituted with a further glycoside, lower alkyl, or lower acyl, e.g. methoxy or acetyloxy. Preferably, at most one such hydroxyl group is substituted with a further glycoside. More preferably, no such hydroxyl group is substituted with a further glycoside; i.e., the substitution is lower acyl, such as acetyl, or lower alkyl, such as methyl. In one embodiment, all of the hydroxyl groups on the glycoside(s) are unsubstituted.

Preferably, a subject compound of formula I, II, or III includes a maximum of three glycosides, more preferably a maximum of two glycosides. In selected embodiments, the compound includes zero, one, or two glycosides, none of which is substituted with a further glycoside. In further selected embodiments, particularly with respect to formula I, the compound includes zero or two glycosides, none of which is substituted with a further glycoside.

In selected embodiments of formula I, each of $X^1$ and $X^2$ is independently selected from hydroxy, lower alkoxy, lower acyloxy, glucopyranoside, and xylopyranoside, and $X^3$ is selected from hydroxy, lower alkoxy, lower acyloxy, keto, glucopyranoside, and xylopyranoside, preferably from hydroxy, lower alkoxy, lower acyloxy, and keto.

In further embodiments of formula I, $X^1$ is selected from hydroxy, lower alkoxy, lower acyloxy, and β-D-xylopyranoside; $X^2$ is selected from hydroxy, lower alkoxy, lower acyloxy, and β-D-glucopyranoside; $X^3$ is selected from hydroxy, lower alkoxy, lower acyloxy, and keto (=O); and $OR^1$ is selected from hydroxy, lower alkoxy, lower acyloxy, and β-D-glucopyranoside.

In further selected embodiments of formula I, $X^1$ is OH or a glycoside, each of $X^2$ and $OR^1$ is independently OH or a glycoside, and $X^3$ is OH or keto. In further embodiments, each of $X^1$ and $X^2$ is OH or a glycoside, $OR^1$ is OH, and $X^3$ is OH. In still further embodiments, $X^1$ is β-D-xylopyranoside, $X^2$ is β-D-glucopyranoside, $OR^1$ is OH, and $X^3$ is OH. In another embodiment, each of $X^1$, $X^2$, $X^3$ and $OR^1$ is OH.

For each of these described embodiments, further embodiments include compounds in which $R^2$ is methyl and ≡ represents a double bond, and other embodiments, generally preferred, include compounds in which $R^2$ forms, with carbon 9, a fused cyclopropyl ring.

Exemplary compounds of structure I for use in the methods of the invention include those shown in FIG. 1, and designated herein as 1 (astragaloside IV), 2 (cycloastragenol), 3 (astragenol), 4 (astragaloside IV 16-one), 6 (cycloastragenol 6-β-D-glucopyranoside), and 7 (cycloastragenol 3-β-D-xylopyranoside).

Other compounds having the backbone structure of cycloastragenol (2) substituted with a 3-β-D-glycopyranoside are also considered for use in the methods of the invention. Preferably, the compound includes a total of one or two glycosides, attached to separate carbons of the backbone structure (i.e. one glycoside is not attached to a further glycoside). Examples include the naturally occurring compounds astragalosides A, 1, 2, and 7, as well as the astraverrucins I and II (which can be isolated from *Astragalus verrucosus*).

In another embodiment, the compounds are represented by formula II,

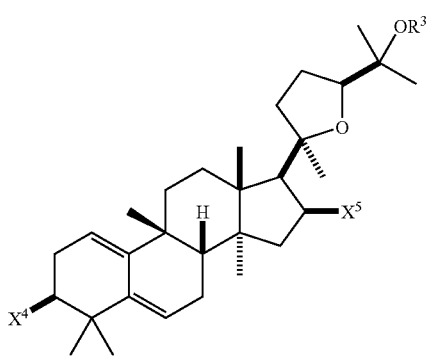

where each of $X^4$ and $X^5$ is independently selected from hydroxy, lower alkoxy, lower acyloxy, keto, and a glycoside, and $OR^3$ is selected from hydroxy, lower alkoxy, lower acyloxy, and a glycoside; where "glycoside" and its various embodiments are as described above. As noted above, the compound includes a maximum of three glycosides, more preferably a maximum of two glycosides. In selected embodiments, the compound includes zero, one, or two glycosides, none of which is substituted with a further glycoside.

In selected embodiments of formula II, $X^4$ is selected from hydroxy, lower alkoxy, lower acyloxy, and a glycoside. In further embodiments, each of $X^4$, $X^5$, and $OR^3$ is independently selected from hydroxy, lower alkoxy, lower acyloxy, glucopyranoside, and xylopyranoside.

In further embodiments of formula II, each of $X^4$ and $OR^3$ is selected from hydroxy, lower alkoxy, lower acyloxy, and a glycoside, preferably D-xylopyranoside or D-glucopyranoside, and $X^5$ is selected from hydroxy, lower alkoxy, lower acyloxy, and keto (=O). Preferably, in these embodiments, $OR^3$ is selected from hydroxy, lower alkoxy, and lower acyloxy, and is more preferably hydroxy.

In further embodiments of formula II, each of $X^4$, $X^5$, and $OR^3$ is independently OH or a glycoside, e.g. D-xylopyranoside or D-glucopyranoside. In still further embodiments, $X^4$ is OH or a glycoside, and each of $X^5$ and $OR^3$ is OH. In one embodiment, each of $X^4$, $X^5$, and $OR^3$ is OH. This compound (formally named 20R,24S-epoxy-3β, 16β,25-trihydroxy-9β-methyl-19-norlanost-1,5-diene) is designated herein as 5.

In another embodiment, the compounds are represented by formula III:

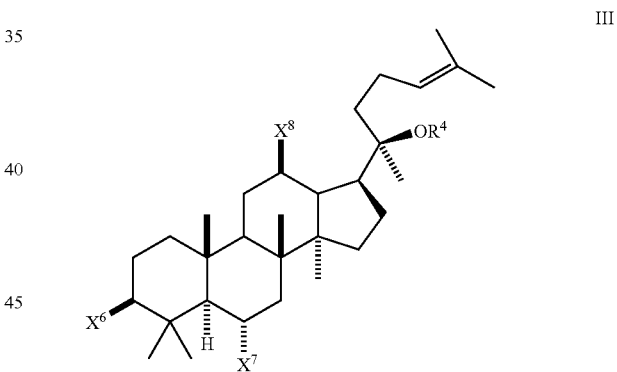

where each of $X^6$, $X^7$, $X^8$ and $OR^4$ is independently selected from hydroxy, lower alkoxy, lower acyloxy, keto, and a glycoside, where "glycoside" and its embodiments are as defined above. Preferably, the compound includes a maximum of two glycosides, more preferably a maximum of one glycoside, none of which is substituted with a further glycoside. Preferred glycosides include D-glucopyranoside and D-xylopyranoside.

In selected embodiments of structure III, each of $X^6$, $X^7$, $X^8$ and $OR^4$ is independently selected from hydroxy, lower alkoxy, lower acyloxy, and a glycoside, and is preferably selected from hydroxy and a glycoside.

In further embodiments of structure III, each of $X^8$ and $OR^4$ is OH, and each of $X^6$ and $X^7$ is independently selected from hydroxyl and a glycoside, e.g. β-D-glucopyranoside. In further embodiments, $OR^4$ is OH. Preferably, each of $X^6$ and $X^8$ is also OH, and $X^7$ is a glycoside. An exemplary compound of structure III is ginsenoside RH1, designated herein as 8.

In selected embodiments, the formulation contains from 0.01 to 10% (w/v) of one or more compounds of structure I, II or III. In other selected embodiments, the formulation contains about 0.01 to 1, or about 0.05 to 5% (w/v) of such a compound or combination of compounds. In one embodiment, the formulation contains at least 0.005% but less than 0.1% (w/v) of such a compound or combination of compounds, e.g., the compound designated herein as 1 or 2 or a combination thereof.

C. Sources and Syntheses of Compounds of Formulas I-III

The compounds of formulas I, II and III can generally be isolated or synthesized from naturally occurring materials. For example, astragalosides I-VII can be isolated from *Astragalus membranaceus* root, as described, for example, in A. Kadota et al., J P Kokai No. 62012791 A2 (1987). As reported therein, the root tissue (8 kg), which is commercially available from various sources of beneficial herbs, is refluxed with MeOH, and the concentrated extract (200 g) is redissolved in MeOH and fractionated by column chromatography on silica gel, using $CHCl_3/MeOH/H_2O$ mixtures as eluants. Each fraction is worked up by reverse chromatography on silica gel, using similar solvent mixtures, to give the following approximate quantities of isolated compounds: acetylastragaloside I (0.2 g), astragaloside I (3.5 g), isoastragaloside I (0.3 g), astragaloside II (2.3 g), astragaloside III (1.0 g), astragaloside IV (0.8 g), astragaloside V (0.1 g), astragaloside VI (0.3 g), and astragaloside VII (0.1 g). See also Kitagawa et al., *Chem. Pharm. Bull.* 31(2):698-708 (1983b).

Astragaloside IV (designated herein as 1) was also obtained by the present authors from Ai Chunmei, Chengdu 610041, P.R. China.

Cycloastragenol (2) can be prepared by treatment of astragaloside IV (1) with methanolic HCl, followed by neutralization, standard workup, and purification by chromatography, as described in the Experimental section below (Example 1). Cycloastragenol can also be obtained by oxidative degradation (treatment with oxygen and elemental sodium) of a butanol extract of *Astragalus membranaceus*, as described by P-H Wang et al., *J. Chinese Chem. Soc.* 49:103-6 (2002). Astragenol (3) and cycloastragenol (2) can also be obtained according to the procedure of Kitagawa et al., *Chem. Pharm. Bull.* 31(2):689-697 (1983a).

The compounds designated herein as 6 (cycloastragenol 6-β-D-glucopyranoside) and 7 (cycloastragenol 3-β-D-xylopyranoside) were obtained by refluxing a solution of astragaloside IV (1) and sulfuric acid in methanol, followed by standard workup and silica gel chromatography, as described in Example 2 below. Also obtained were the rearrangement product 5 and the aglycone, i.e. cycloastragenol (2).

The 16-keto compound 4 was prepared by acetylation of the glycoside hydroxyl groups of astragaloside IV, followed by pyridinium chlorochromate oxidation of the 16-hydroxyl, and restoration of the glycoside hydroxyls by treatment with sodium borohydride (see Kitagawa et al., 1983b, cited above). Preparation of the various embodiments of formulas I-III, e.g. compounds having varying degrees of alkylation or acylation, or keto groups, can be prepared according to known methods of organic synthesis, using naturally occurring and/or commercially available starting materials such as cycloastragenol, astragenol, the astragalosides or astraverrucins, or panaxatriol, with separation of products as needed. Several examples are given in the Experimental section below. For example, the less sterically hindered 3-, 6-, and/or 16-hydroxyl groups can generally be selectively modified, e.g. by acylation. If desired, the unreacted hydroxyl groups can then be separately modified, e.g. by alkylation, followed by optional removal of the acyl groups. Compounds of formula I having a fused cyclopropyl ring (e.g. cycloastragenols) can be converted to compounds having a 19-methyl group and 9-11 double bond (e.g. astragenols) by sulfuric acid treatment. This reaction may be accompanied by deglycosylation, as shown in the reactions of Examples 9B and 10B, below.

D. Methods of Application

A formulation of a compound or extract as described above, in a cosmetic vehicle such as described above, is applied in an amount and frequency effective to obtain the desired effects, which include, for example, diminishing roughness and dryness of the skin, diminishing or preventing wrinkling, and preventing or alleviating damage of skin by UV radiation.

Quantities of the formulation applied per application can vary, but typically range from about 0.1 to about 10 mg/cm$^2$ of skin surface. In one embodiment, the formulation is applied daily, to areas such as the face, hands, arms, or feet; however, application rates can vary from about once per week up to about three times per day or more. The compositions may also be applied, generally in the form of a skin lotion or cream, to be left on the skin for an extended period such as one or more hours, for some aesthetic, prophylactic, or other benefit (i.e., a "leave-on" composition).

Bioavailability of the subject compounds in topical administration was assessed by determining the percutaneous absorption of cycloastragenol (2) in a human cadaveric skin model (T. J. Franz et al., *Abst. J Invest Dermatol* 94:525, 1990). Three concentrations (0.01, 0.05 and 0.25 wt % in 5 µL volumes) of tritium-labeled compound, in petrolatum or hydrogel formulations, were applied to 0.8 cm$^2$ skin surface, resulting in outer skin exposures ranging from about 0.6 to 15 µg/cm$^2$. The receptor solution concentration (representing the inner surface of the skin) was then collected at predetermined intervals over 48 hours, to determine extent and rate of appearance of labeled compound. The total delivery over 48 hours ranged from ~66 ng in the lowest concentration hydrogel formulation to ~600 ng in the highest concentration petrolatum formulation, suggesting saturation of transport.

III. Biological Activity of Subject Compounds

The compounds disclosed herein for use in the methods of the invention are active, as demonstrated below, in inducing telomerase activity in normal cells. Such activity is expected to provide benefits in reducing signs of aging in skin cells, e.g. by inhibiting cell death during proliferation and thus promoting cell growth.

A. TRAP Assay Protocol

The ability of a compound to increase telomerase activity in a cell can be determined using the TRAP (Telomeric Repeat Amplification Protocol) assay, which is known in the art (e.g. Kim et al., U.S. Pat. No. 5,629,154; Harley et al., U.S. Pat. No. 5,891,639, which are incorporated herein by reference). As used herein, "telomerase activity as measured in a TRAP assay" refers to telomerase activity as measured in keratinocytes or fibroblasts according to the following protocol. The activity is typically compared to the activity similarly measured in a control assay of such cells (e.g., a telomerase activity 25% greater than observed in a solvent control).

Cell lines suitable for use in the assay, preferably normal human fibroblasts (NHF) or normal human keratinocytes (NHK), can be obtained from commercial sources, such as Cascade Biologics, Portland, Oreg. or 4C Biotech, Seneffe, Belgium, or from the ATCC (American Type Culture Collection). ATCC normal human fibroblast cell lines, which can be located on the ATCC web site, include, for example, CCL135, CCL137, and CCL151.

Cells are plated at approx. 5000 cells/well, in growth medium (e.g. Epi-Life Medium+Keratinocyte Growth Factor Supplement+60 mM CaCl$_2$, supplied by Cascade Biologics, Inc.) for two days. Test compositions in a suitable solvent, such as 95% ethanol or DMSO, are added to selected wells in a range of concentrations and incubated for 16-24 hours. For the data reported herein, the solvent used was DMSO.

Cell lysing solution is prepared by addition of 3.0 mL Nonidet® P40, 1.0 mL CHAPS lysis buffer (see below), and 1.0 mL 10× TRAP buffer (see below) to 5.0 mL DNase-, RNase-free H$_2$O. (DNase-, RNase-free water may be generated by DEPC (diethylpyrocarbonate) treatment or purchased from vendors such as Sigma.)

The morphology of treated cells is first observed under a microscope, to verify that there are no visual signs of irregular growth. Media is removed from the wells, and the cells are rinsed twice in PBS (Ca and Mg free). The dishes are chilled, preferably on ice, and cell lysis buffer (see below) is added (approx. 100 μl per well) and triturated by pipetting up and down several times. The cells are the incubated on ice for 1 hour.

CHAPS Lysis Buffer

| Stock | For 1 mL | Final concn. |
|---|---|---|
| 1 M Tris-HCl pH 7.5 | 10 μl | 10 mM |
| 1 M MgCl$_2$ | 1 μl | 1 mM |
| 0.5 M EGTA | 2 μl | 1 mM |
| 100 mM AEBSF | 1 μl | 0.1 mM |
| 10% CHAPS$^a$ | 50 μl | 0.5% |
| BSA | 1 mg | 1 mg/ml |
| 100% Glycerol | 100 μl | 10% |
| DNase-, RNase-free H$_2$O | 936 μl (to 1 mL) | |

$^a$The CHAPS detergent should be added just before use of the lysis buffer. In addition, AEBSF (4-(2-aminoethyl)-benzenesulfonyl fluoride hydrochloride) should be added to the lysis buffer just prior to performing the extraction step.

10× TRAP Buffer

| Stock | For 5 ml | Final concn. |
|---|---|---|
| 1 M Tris-HCl, pH 8.3 | 1 ml | 200 mM |
| 1 M MgCl$_2$ | 75 μl | 15 mM |
| 1 M KCl | 3.15 ml | 630 mM |
| Tween 20 (Boehringer Mannheim) | 25 μl | 0.5% |
| 0.1 M EGTA | 500 μl | 10 mM |
| 20 mg/ml BSA | 250 μl | 1 mg/ml |

The following materials are combined to generate a master PCR Mix.

| Stock | Per Reaction (40 μl) | Final concn.$^a$ |
|---|---|---|
| 10× TRAP Buffer | 5.0 μl | 1× |
| 2.5 mM dNTPs | 1.0 μl | 50 μM |
| Cy5-TS Primer (0.1 mg/ml) | 0.2 μl | 0.4 ng/ml |
| ACX Primer (0.1 mg/ml) | 1.0 μl | 2 ng/ml |
| TSU2 Int. Std. (1 pg/ml) | 1.0 μl | 20 fg/ml |
| U2 Primer (0.1 mg/ml) | 1.0 μl | 2 ng/ml |
| Taq Polymerase (5 U/μl) | 0.4 μl | 2 units |
| DNase-, RNase-free H$_2$O | 30.4 μl (to 40 μl total) | |

$^a$Based on final volume of 40 μl PCR mix plus 10 μl cell lysate = 50 μl.

The PCR mix includes the following components: Cy5-TS primer, a 5'-Cy5 labeled oligonucleotide having the sequence 5'-AAT CCG TCG AGC AGA GTT-3' (SEQ ID NO: 1), is a telomerase substrate. Depending on the telomerase activity of the medium, telomer repeats (having the sequence . . . AGGGTT . . . ) will be added to the substrate, to form telomerase extended products, also referred to as telomerase products or TRAP products. The ACX primer, having the sequence 5'-GCG CGG CTT ACC CTT ACC CTT ACC CTA ACC-3' (SEQ ID NO: 2), is an anchored return primer that hybridizes to the telomerase extended products.

The TSU2 internal standard, an oligonucleotide having the sequence 5'-AAT CCG TCG AGC AGA GTT AAA AGG CCG AGA AGC GAT-3'; SEQ ID NO:3), an extension of the TS primer sequence, is added in a small controlled quantity for quantitation purposes. The U2 primer, having the sequence 5'-ATC GCT TCT CGG CCT TTT (SEQ ID NO:4), is a return primer designed to hybridize to the 3' region of the internal standard.

A sample of cell lysate (10 μL) is added to 40 μL of this PCR mix in a reaction tube, and the mixture is incubated at room temperature (30° C.) for 30 minutes. PCR is carried out by incubating the mixture at the following temperatures for the times indicated: 94° C./30 sec, 60° C./30 sec, and 72° C./30 sec; repeating this three-step cycle to conduct 20-30, preferably 31 cycles.

Loading dye containing e.g. bromophenol blue and xylene cyanol is added, and the samples are subjected to 10-15% non-denaturing PAGE in 0.6× TBE, until the bromophenol blue runs off the gel. Product formation is observed, e.g. by using a fluoroimager for detection of CY5-labeled telomerase products (maximal excitation at 650 nm; maximal emission at 670 nm).

The final amount of TSU2 internal standard after amplification is generally 5-10 amol per 50 μl reaction mixture. This internal control gives a specific 36-mer PCR amplification product that appears as a distinct band on the gel below the first telomer addition product (that is, the product of one telomer addition to the TS oligonucleotide, followed by amplification with the ACX return primer). This internal control band can be used to normalize the PCR amplifications from different samples.

The relative number of telomerase product molecules (TM) generated in the assay is determined according to the formula below:

$$TM = (T_{TRAP\ Products} - T_{BKD1})/(T_{Int\ Std} - T_{BKD2})$$

where: $T_{TRAP\ Products}$ is the total intensity measured on the gel for all telomerase products, $T_{BKD1}$ is the background intensity measured in a blank lane for an area equivalent in size to that encompassed by the telomerase products, $T_{Int\ Std}$ is the intensity for the internal standard band, and $T_{BKD2}$ is the background intensity measured in a blank lane for an area equivalent in size to that encompassed by the internal standard band. The resulting number is the number of molecules of telomerase products generated for a given incubation time, which, for the purposes of determining TM, is designated herein as 30 minutes.

Preferred compounds of formula I, II or III for use in the methods and formulations described herein are effective to produce, at a concentration of 1 μg/ml, a telomerase activity at least about 25% greater than a solvent control, and more preferably at least about 50% greater than a solvent control, as measured in the described TRAP assay. Even more potent activities may be appropriate for some applications, such as compounds that produce, at concentrations of 1 μg/ml or less, a telomerase activity which is at least about 75%, 100% or 500% greater than a solvent control.

B. Exemplary TRAP Assay Results

Figure 2:
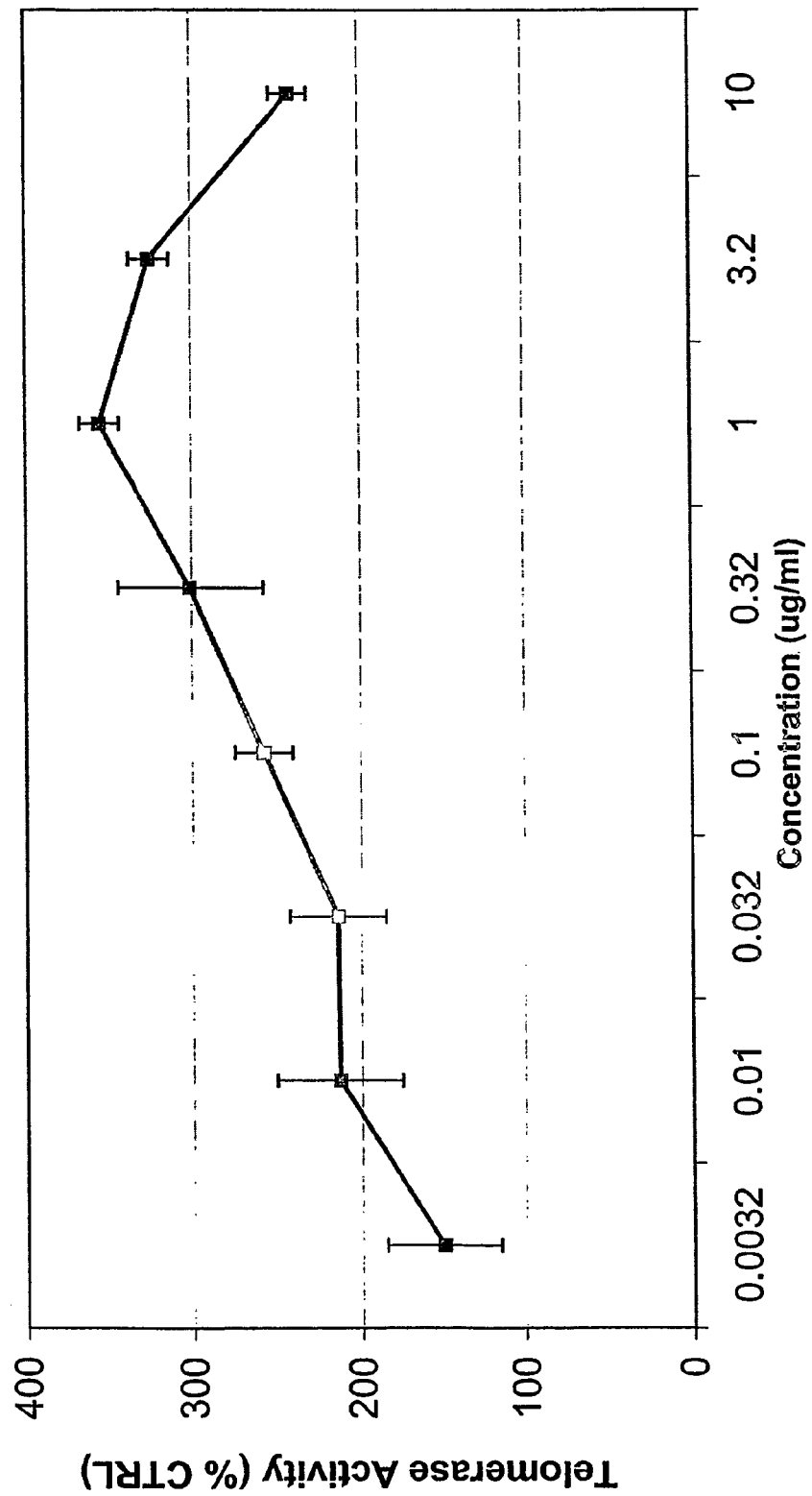
FIG. 2 shows an increase of telomerase activity in neonatal keratinocytes treated with 2 (cycloastragenol), as measured in a TRAP assay.
Figure 3:
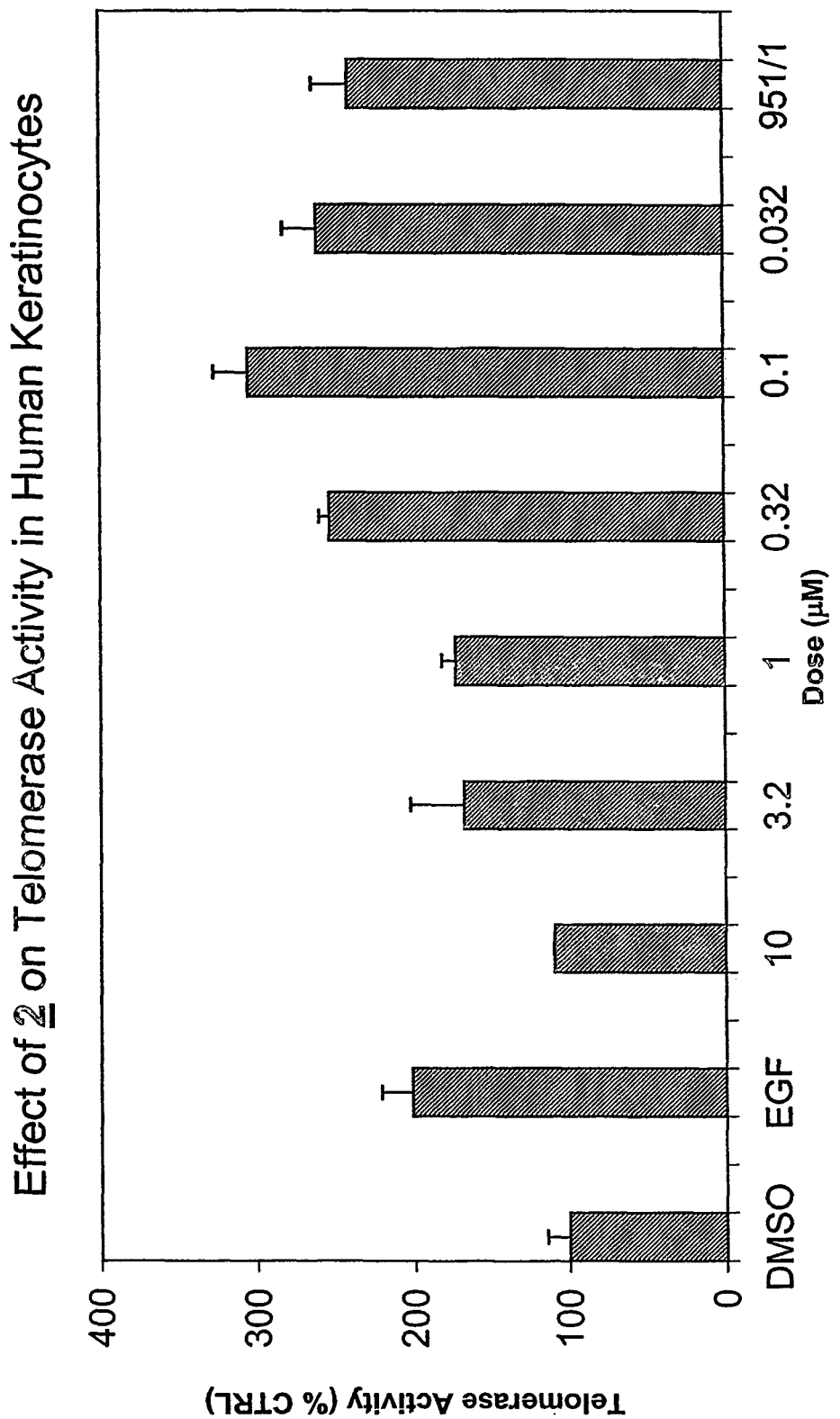
FIG. 3 shows an increase in telomerase activity in neonatal keratinocytes by 1 (astragaloside IV), in comparison with EGF (10 nM) and a solvent control, as measured in a TRAP assay.

Effectiveness in increasing telomerase activity was evaluated for selected compounds of formulas I-III in various concentrations. Assays were carried out in vitro in HEKneoP cells (neonatal keratinocytes), according to the protocol described above. Concentrations ranged from approx. 0.03 to 10 μM. As shown in FIG. 2, for 1 (astragaloside IV), telomerase activity increased with increasing concentration, up to about 360% of control at 1.0 μM, then decreased as the concentration was increased further to 10 μM. As shown in FIG. 2, for 2 (cycloastragenol), telomerase activity increased to about 300% of control at 0.1 μM (compared to about 200% in cells treated with 10 nM EGF (epidermal growth factor)), then decreased with further increases in concentration.

Table 1 gives, for each of the compounds shown in FIGS. 1A-G, the minimum effective concentration (MEC) producing a level of telomerase activity twice that seen in a DMSO control (i.e. 100% greater).

TABLE 1

| Designation | Name | MEC, μM |
|---|---|---|
| 1 | astragaloside IV | 0.01 |
| 2 | cycloastragenol | 0.01 |
| 3 | astragenol | 0.03 |
| 4 | astragaloside IV 16-one | 0.03 |
| 5 | 20R,24S-epoxy-3β,16β,25-trihydroxy-9β-methyl-19-norlanost-1,5 -diene | 0.10 |
| 6 | cycloastragenol 6-β-D-glucopyranoside | 3.2 |
| 7 | cycloastragenol 3-β-D-xylopyranoside | 3.2 |
| 8 | ginsenoside RH1 | 10 |

C. Cell Proliferation Assay Protocol

Promotion of cell proliferation by the compounds can be evaluated, preferably in keratinocytes or fibroblasts as described above, via a "scratch assay", carried out as follows. As used herein, "as measured in a scratch assay" refers to measurement of cell reconfluence in keratinocytes or fibroblasts according to the following protocol, and expressed as the value of SC shown in the formula below.

Cells are plated in flasks ($(5 \times 10^5$ cells per flask) and cultured for two days in a humidified chamber at 5% $CO_2$, 37° C. A 2 ml plastic pipette is gently dragged thought the culture to "scratch" the cell surface. The ideal scratch is approximately 2-3 mm wide and 50 mm long (along the long axis of the tissue culture flask). The cells are retreated with medium containing either vehicle (control sample) or test compositions at multiple dilutions. A scratch area is identified, the flask marked, and the appearance of the cells documented photographically over 3-4 days continued culturing of the cells.

Amount of cell reconfluence, or closure of the scratch, is determined by measuring width of the scratch over time for compound-treated samples relative to vehicle-treated or other control cells. Measurements are made from the photographs taken for each of the samples on days 0, 1, 2, and 3. Percentage of closure is calculated by the following formula:

$$SC=100-[100 \times W_n/W_0],$$

where $W_n$ is the width of the scratch on day n and $W_0$ is the width of the scratch on day one (i.e. immediately after scratching).

Preferred compounds of formulas I-III for use in the cosmetic methods and formulations described herein are able to produce, at a concentration of 1 μg/ml or less, an amount of closure in a scratch assay of keratinocytes or fibroblasts which is at least 25% greater than that seen in untreated or control cells. Even more potent activities may be appropriate for some applications, such as compounds that produce, at concentrations of 1 μg/ml or less, an amount of closure in a scratch assay of keratinocytes or fibroblasts which is at least about 75%, 100% or 500% greater than that seen in untreated or control cells.

D. Exemplary Scratch Assay Results

Promotion of cell proliferation by 1 (astragaloside IV) and for 2 (cycloastragenol) was evaluated in aging keratinocytes via a scratch assay, as described above. Briefly, a scratch, typically about 2-3 mm in width, is created through a mass of plated cells, and the time needed for the cells to become confluent is observed.

Figure 4:
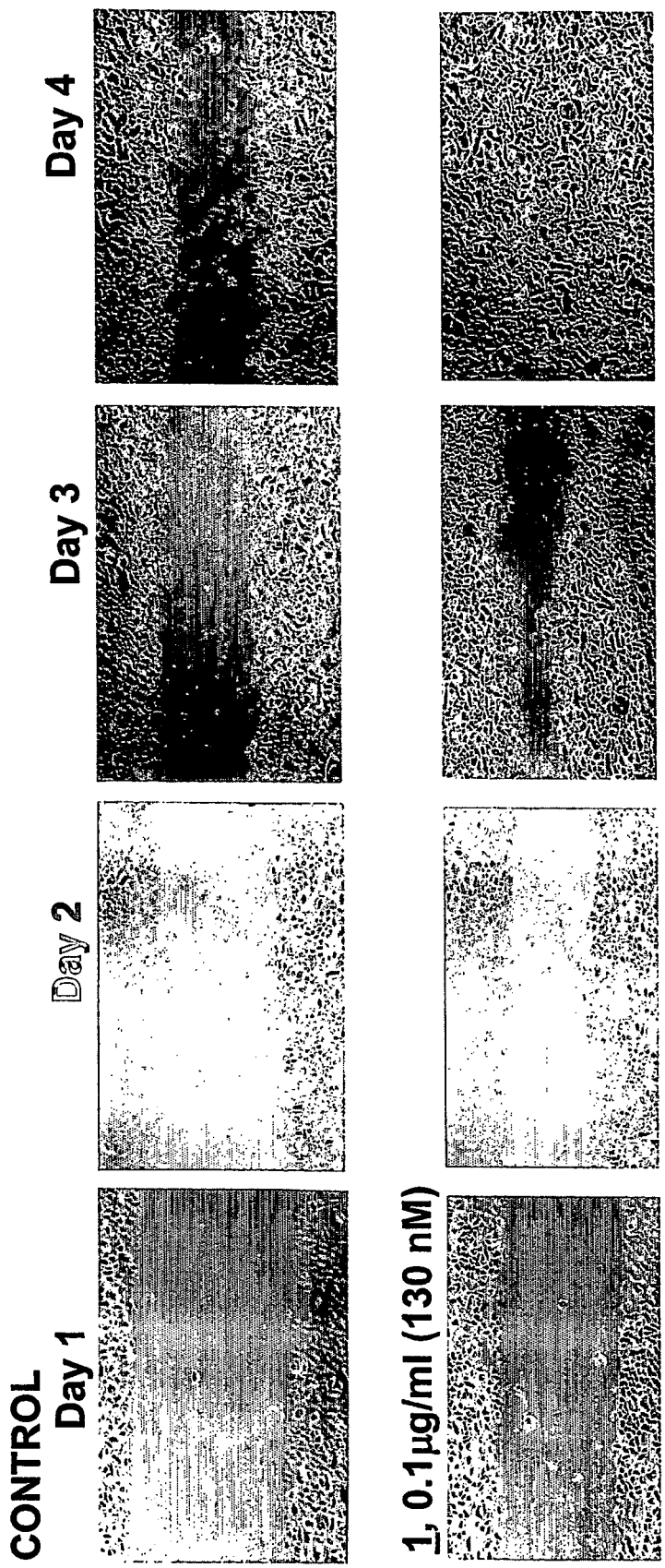
FIG. 4 is a series of computer-generated images showing activity of 1 (astragaloside IV) in a "scratch assay" of aging adult keratinocytes.
Figure 5:
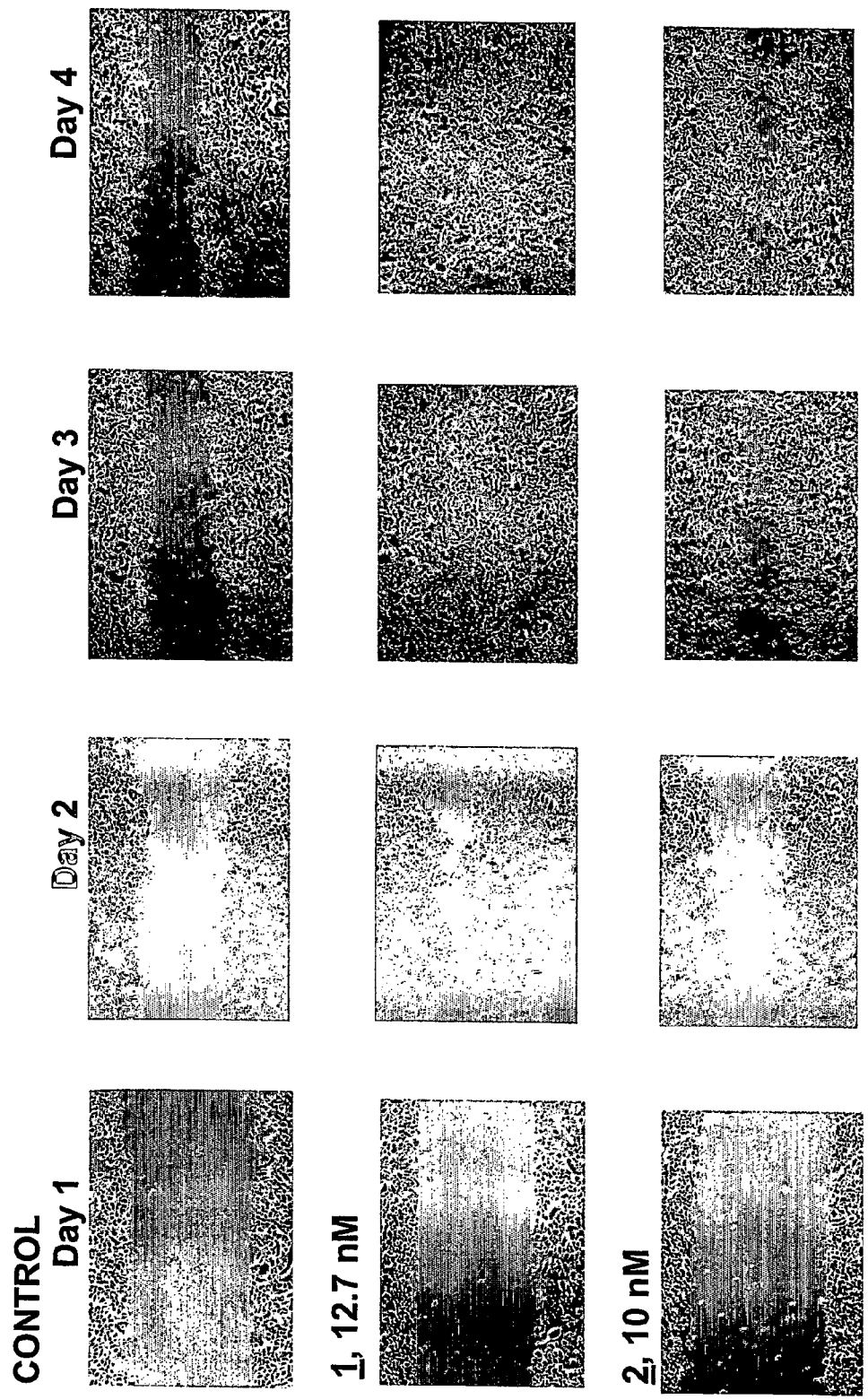
FIG. 5 is a series of computer-generated images showing activity of 1 (astragaloside IV) and 2 (cycloastragenol) in a scratch assay of young neonatal keratinocytes.

Results of a typical assay are shown in FIG. 4, where the top row of images shows control cells, and the bottom row shows cells treated with 0.1 μg/ml (about 0.13 μM) 1. The treated cells were confluent at day 4, in contrast to the control cells, in which a significant area of the original scratch remained at day 4. Similar results were seen with this compounds and with 0.01 μM 2 (cycloastragenol) in young keratinocytes, as shown in FIG. 5.

Figure 6:
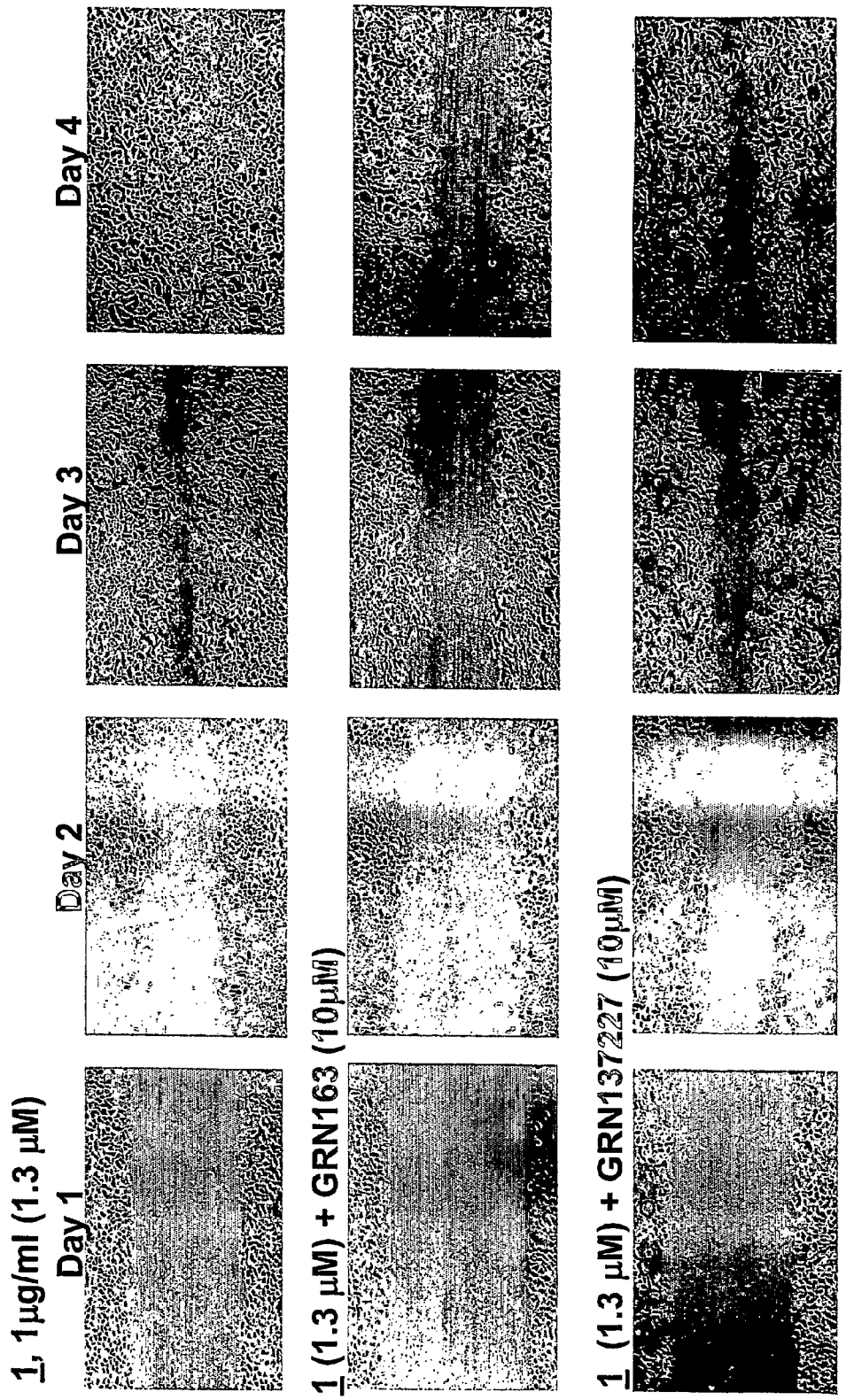
FIG. 6 is a series of computer-generated images showing activity of 1 (astragaloside IV) in a scratch assay or aging adult keratinocytes, alone and in the presence of a telomerase inhibiting oligonucleotide (GRN163) or a control oligonucleotide (GRN137227)

FIG. 6 shows promotion of cell proliferation by 1 (astragaloside IV) in aging adult keratinocytes, as measured in a similar assay, alone and in the presence of a telomerase inhibiting oligonucleotide (GRN163) or a control oligonucleotide (GRN137227). As shown, telomerase inhibiting oligo GRN163 blocks the effects of 1; the effect of control oligo GRN137226 is minimal. (GRN163 is a telomerase inhibitor oligonucleotide that targets the template region of the telomerase RNA component. Specifically, GRN163 is a 13-mer N3'→P5' thiophosphoramidate oligonucleotide, described in detail in PCT Pubn. No. WO 01/18015. GRN137227 is a 13-mer N3'→P5' thiophosphoramidate control oligonucleotide having a mismatched sequence.)

Table 2 below shows SC values for compounds 1 and 2 employed in the scratch assays shown in FIGS. 5 and 6, and for solvent controls, based on the results of those assays, and using the formula shown above.

TABLE 2

| | Approx. scratch width (arbitrary units) | | | | | |
|---|---|---|---|---|---|---|
| | Day 1 cntl | Day 4 cntl | Day 1 test | Day 1 test | $SC_{cntrl}$ | $SC_{test}$ |
| FIG. 4 (1) | 22 | 10 | 17 | 0 | 54.5 | 100 |
| FIG. 5 (1) | 19 | 9 | 18 | 0 | 52.6 | 100 |
| FIG. 5 (2) | 19 | 9 | 21 | 2 | 52.6 | 90.5 |

FIG. 7 graphically illustrates promotion of cell reconfluence by 1 (astragaloside IV) in aging neonatal keratinocytes, in the presence and absence of a telomerase inhibitor (GRN163), and in comparison with 50 ng/mL (approx. 2 mL) PDGF (platelet derived growth factor). As shown, promotion of cell reconfluence by 1 was comparable to that of PDGF, and was again blocked by the addition of GRN163.

EXAMPLES

The following examples are intended to illustrate but not to limit the invention.

Example 1

Conversion of Astragaloside IV (1) to Cycloastragenol (2)

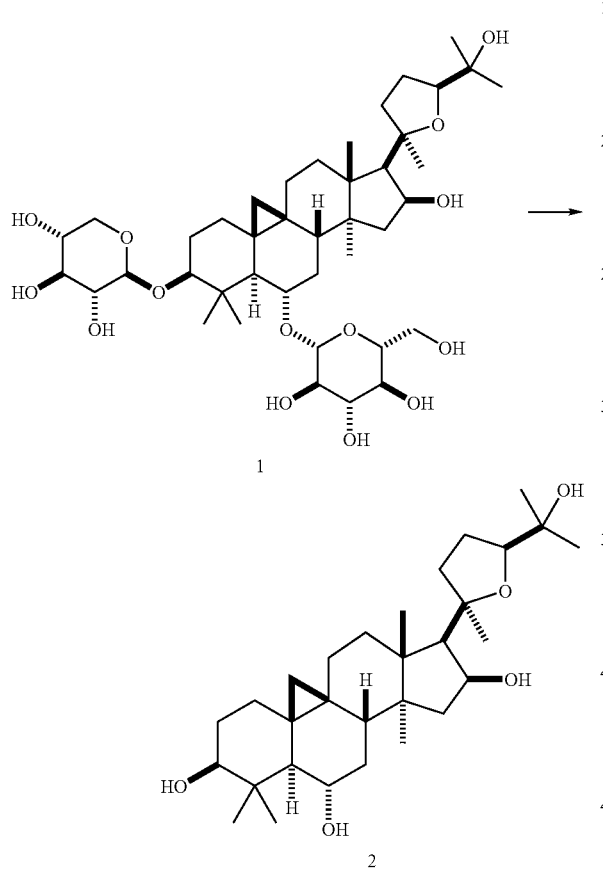

To astragaloside IV (1) (5.00 g, mmol) was added "HCl-MeOH 10" (TCI America) (500 mL) and the mixture was stirred at room temperature for 7 days. The reaction mixture was concentrated to about half volume under reduced pressure at 20° C. (do not heat). The mixture was partitioned into aqueous sodium bicarbonate and ethyl acetate. The aqueous layer was extracted with ethyl acetate again. The organic layers were combined, washed with saturated sodium chloride, dried on anhydrous sodium sulfate, and concentrated under reduced pressure. The residue was purified by column chromatography (20:1~14:1 chloroform/methanol). In order to replace the residual solvent with ethanol, the purified material was dissolved in ethanol and the solvent was removed under reduced pressure to afford 2 (2.1 g, 64%).

$^1$H NMR (CDCl$_3$) δ (ppm) 0.34 (d, J=4.7 Hz, 1H), 0.48 (d, J=4.3 Hz, 1H), 0.92 (s, 3H), 0.93 (s, 3H), 1.0-1.8 (m, 13H), 1.11 (s, 3H), 1.19 (s, 3H), 1.22 (s, 6H), 1.27 (s, 3H), 1.9-2.0 (m, 4H), 2.30 (d, J=7.8 Hz, 1H), 2.54 (q, J=11.8 Hz, 1H), 3.27 (m, 1H), 3.50 (m, 1H), 3.72 (t, J=7.4 Hz, 1H), 4.65 (q, J=7.4 Hz, 1H). ESI-MS m/z Positive 491 (M+H)$^+$, Negative 549 (M+AcO)$^-$. TLC (Merck, Kieselgel 60) Rf=0.33 (6:1 chloroform/methanol).

Example 2

Preparation of Compounds 5, 6 and 7 from Astragaloside IV (1): Removal of Glycosides from Astragaloside IV (1), with and without Concomitant Rearrangement

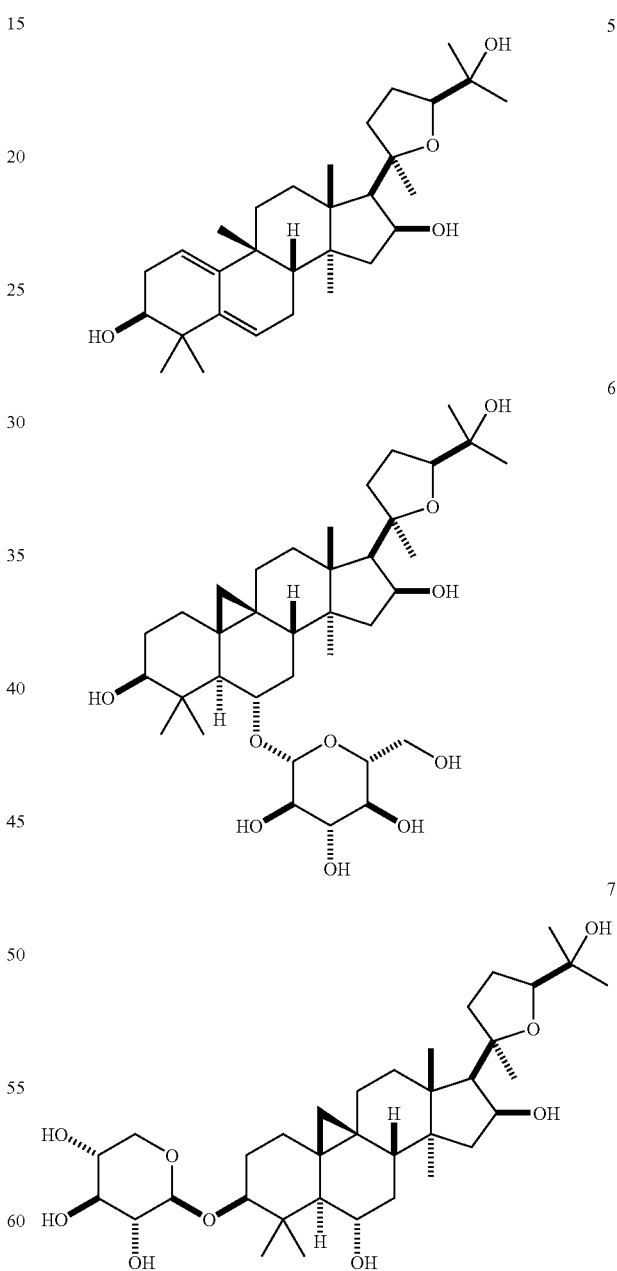

To a solution of astragaloside IV (1, 1.00 g, 1.28 mmol) in methanol (80 mL) was added sulfuric acid (0.4 mL), and the mixture was refluxed for 1.5 h. After cooling to room temperature, the mixture was poured into ethyl acetate and water.

The organic layer was washed with brine and dried on anhydrous sodium sulfate. The solvent was removed under reduced pressure, and the residue was purified by silica gel column chromatography (20:1~10:1~7:1 chloroform/methanol) to afford the rearranged product 5 (24 mg, 4.0%), monoglycosides 6 (172 mg, 21%) and 7 (29 mg, 3.6%) and the aglycone, cycloastragenol (2) (326 mg, 52%).

GRN140724: ESI-MS m/z 623 (M+H)$^+$ $C_{35}H_{58}O_9$=622
GRN140725: ESI-MS m/z 653 (M+H)$^+$ $C_{36}H_{60}O_{10}$=652
GRN140726: ESI-MS m/z 473 (M+H)$^+$ $C_{30}H_{48}O_4$=472.

$^1$H NMR (400 MHz, CDCl$_3$) δ (ppm) 0.72, 0.85, 0.95, 1.05, 1.11, 1.17, 1.18, and 1.25 (s, 3H each), 0.9-2.1 (n, 13H), 2.20 (d, J=7.4 Hz, 1H), 2.4-2.6 (m, 2H), 3.42 (m, 1H), 3.70 (dd, J=7.8, 5.9 Hz, 1H), 4.63 (q, J=7.4 Hz, 1H), 5.45 (br s, 1H), 5.57 (br s, 1H).

Example 3

Acetylation of 1: Formation of 16-Ketone 10

Compounds 9 and 10, below, were obtained according to the method of Kitagawa 1983b, cited above. Briefly, acetylation of astragaloside IV (1) provided 9, together with a smaller amount of the 16-acetate counterpart. Pyridinium chlorochromate oxidation of 9 gave 10.

Example 4

Preparation of 4 (see FIG. 1) by Deacylation of 10

To a solution of 10, above (10 mg, 0.0093 mmol) in methanol was added sodium borohydride (10 mg, 0.26 mmol), and the mixture was stirred at room temperature overnight. The mixture was diluted with chloroform (3 mL) and directly subjected to silica gel column chromatography (3:1 chloroform/methanol) to afford 4 (8.0 mg, quant.).

ESI-MS m/z 783 (M+H)$^+$ $C_{41}H_{66}O_{14}$=782.

Example 5

Formation of Trione 11 of Cycloastragenol 2

The 3,6,16-trione derivative 11 of cycloastragenol was obtained by CrO$_3$ oxidation of 2, according to the method of Kitagawa et al., *Chem. Pharm. Bull.* 31(2):689-697

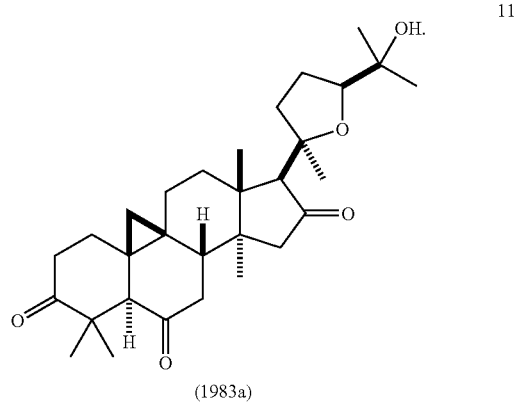

(1983a)

Example 6

Acylation of 3- or 6-Hydroxyl Group of Cycloastragenol (2)

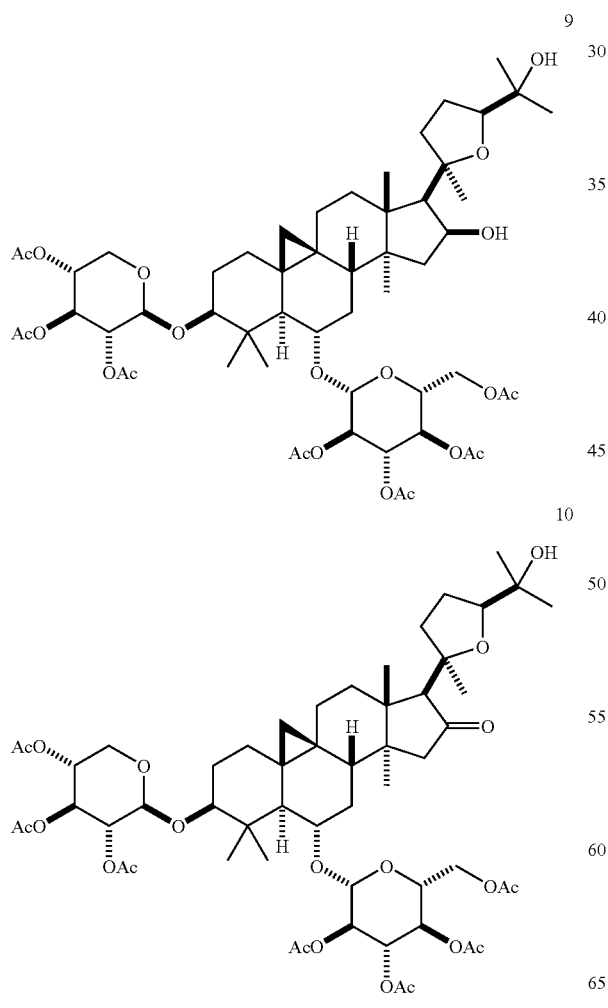

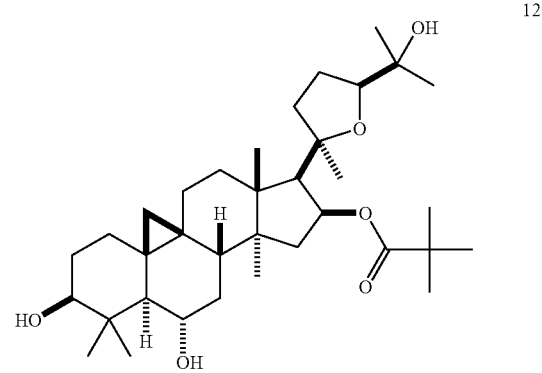

13

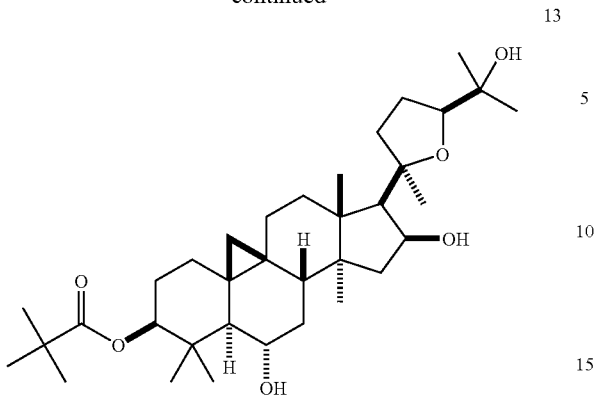

To a solution of cycloastragenol (2) (50 mg, 0.10 mmol) in dichloromethane (5 mL) were added triethylamine (0.030 mL, 0.22 mmol) and pivaloyl chloride (0.014 mL, 0.12 mmol), and the mixture was stirred at 0° C. overnight. The mixture was directly subjected to silica gel column chromatography (1:1~1:2 hexane/ethyl acetate) to give 12 (17 mg, 30%) and 13 (3.3 mg, 2.9%).

12: ESI-MS m/z 575 (M+H)$^+$ $C_{35}H_{58}O_6$=574. $^1$H NMR (400 MHz, CDCl$_3$) δ (ppm) 0.32 (d, J=4.7 Hz, 1H), 0.49 (d, J=4.7 Hz, 1H), 0.92 (s, 3H), 0.95 (s, 3H), 1.07 (s, 3H), 1.1-2.0 (m, 17H), 1.15 (s, 9H), 1.18 (s, 3H), 1.21 (s, 3H), 1.34 (s, 6H), 2.19 (dd, J=13.7, 9.8 Hz, 1H), 2.36 (d, J=7.8 Hz, 1H), 3.27 (m, 1H), 3.51 (td, J=9.4, 3.5 Hz, 1H), 3.71 (t, J=7.4 Hz, 1H), 5.32 (td, J=7.8, 4.7 Hz, 1H).

13: ESI-MS m/z 575 (M+H)$^+$ $C_{35}H_{58}O_6$=574. $^1$H NMR (400 MHz, CDCl$_3$) δ (ppm) 0.35 (d, J=4.3 Hz, 1H), 0.51 (d, J=4.3 Hz, 1H), 0.92 (s, 3H), 1.0-2.0 (m, 17H), 1.03 (s, 3H), 1.09 (s, 3H), 1.12 (s, 3H), 1.17 (s, 9H), 1.21 (s, 3H), 1.24 (s, 3H), 1.28 (s, 3H), 2.29 (d, J=7.8 Hz, 1H), 2.53 (m, 1H), 3.50 (m, 1H), 3.73 (t, J=7.2 Hz, 1H), 4.50 (dd, J=10.9, 4.3 Hz, 1H), 4.65 (m, 1H).

Example 7

A Acetylation of Secondary Hydroxyls of Cycloastragenol (2)

This reaction was carried out according to the method of Kitagawa 1983a, cited above. Briefly, acetylation with acetic anhydride/pyridine gave a mixture of 14 (major product) and 15 (minor product).

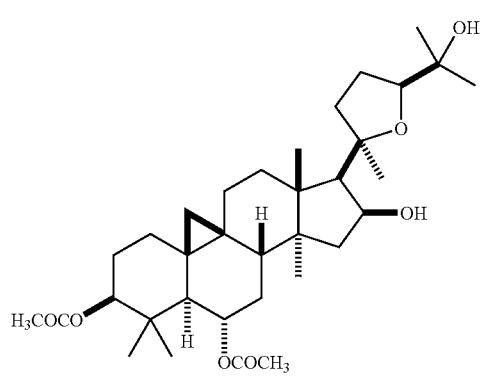

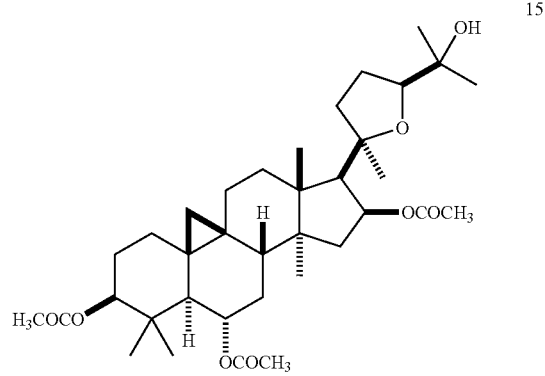

Example 7B

Methylation of 3,6-diacetyl Cycloastragenol (14), with Retention of Acetyl Groups

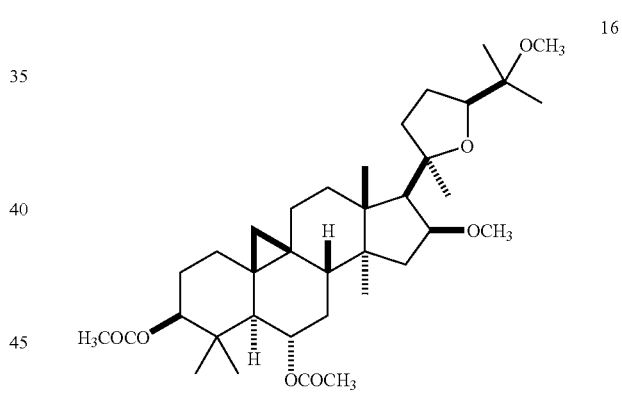

To a solution of 14 (30 mg, 0.052 mmol) in dimethylformamide (3 mL) were added iodomethane (0.75 mL, 12 mmol) and sodium hydride (60% oil dispersion, 40 mg, 1.0 mmol) at 0° C. under nitrogen, and the mixture was stirred at room temperature overnight. Water was added, and the mixture was extracted with ethyl acetate. The organic layer was washed with water and brine and dried on anhydrous sodium sulfate. The solvent was removed under reduced pressure. and the residue was purified by silica gel column chromatography (4:1 hexane/ethyl acetate) to afford the compound 16 (29 mg, 92%).

ESI-MS m/z 603 (M+H)$^+$ $C_{36}H_{58}O_7$=602. $^1$H NMR (400 MHz, CDCl$_3$) δ (ppm) 0.33 (d, J=4.7 Hz, 1H), 0.56 (d, J=4.7 Hz, 1H), 0.82 (s, 3H), 0.89 (s, 3H), 0.96 (s, 3H), 1.06 (s, 3H), 1.1-1.9 (m, 17H), 1.13 (s, 3H), 1.19 (s, 3H), 1.23 (s, 3H), 1.97 (s, 3H), 2.02 (s, 3H), 2.3-2.4 (m, 2H), 3.05 (s, 3H), 3.23 (s, 3H), 3.81 (dd, J=9.0, 6.6 Hz, 1H), 3.95 (td, J=7.8, 5.1 Hz, 1H), 4.54 (dd, J=10.9, 4.7 Hz, 1H), 4.70 (td, J=9.4, 4.3 Hz, 1H).

Example 7C

Preparation of 16,25-dimethoxy Cycloastragenol, 17: Removal of Acetyl Groups from 16

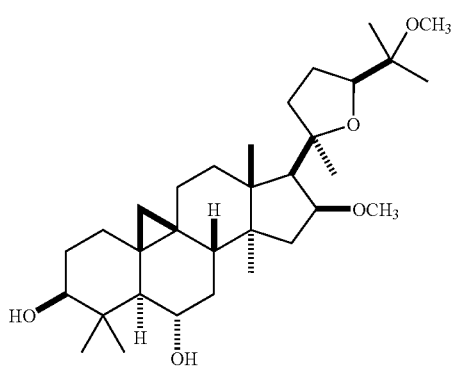

A mixture of 16 (28 mg, 0.046 mmol) and sodium methoxide (0.5 mol/L in methanol, 6 mL) was stirred at room temperature for 48 h. Water was added, and the mixture was extracted with ethyl acetate. The organic layer was washed with water and brine and dried on anhydrous sodium sulfate. The solvent was removed under reduced pressure, and the residue was purified by silica gel column chromatography (2:3 hexane/ethyl acetate) to afford the dimethoxy diol compound 17 (23 mg, 96%).

ESI-MS m/z 519 (M+H)$^+$ C$_{32}$H$_{54}$O$_5$=518. $^1$H NMR (400 MHz, CDCl$_3$) δ (ppm) 0.32 (d, J=4.7 Hz, 1H), 0.47 (d, J=4.3 Hz, 1H), 0.90 (s, 3H), 0.93 (s, 3H), 1.06 (s, 3H), 1.1-1.9 (m, 17H), 1.13 (s, 3H), 1.20 (s, 3H), 1.22 (s, 3H), 1.23 (s, 3H), 2.3-2.4 (m, 2H), 3.06 (s, 3H), 3.23 (s, 3H), 3.27 (m, 1H), 3.51 (td, J=9.4, 3.5 Hz, 1H), 3.81 (dd, J=9.4, 6.6 Hz, 1H), 3.96 (td, J=7.8, 5.5 Hz, 1H).

Example 7D

Alkylation of 3,6-diacetyl Cycloastragenol (14), with Retention of Acetyl Groups

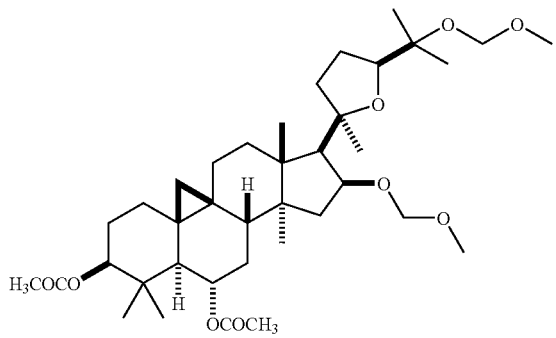

To a solution of 14 (109 mg, 0.190 mmol) in dichloromethane (10 mL) were added diisopropylethylamine (1.0 mL) and chloromethyl methyl ether (0.5 mL), and the mixture was stirred at room temperature for 24 h. Water was added, and the mixture was extracted with ethyl acetate. The organic layer was washed with water and brine and dried on anhydrous sodium sulfate. The solvent was removed under reduced pressure, and the residue was purified by silica gel column chromatography (3:1 hexane/ethyl acetate) to give the compound 18 (114 mg, 90%).

$^1$H NMR (400 MHz, CDCl$_3$) δ (ppm) 0.31 (d, J=5.1 Hz, 1H), 0.56 (d, J=4.7 Hz, 1H), 0.80 (s, 3H), 0.88 (s, 3H), 0.96 (s, 3H), 1.1-2.0 (m, 18H), 1.15 (s, 3H), 1.17 (s, 3H), 1.28 (s, 3H), 1.34 (s, 3H), 1.96 (s, 3H), 2.02 (s, 3H), 2.28 (d, J=8.2 Hz, 1H), 3.30 (s, 3H), 3.33 (s, 3H), 3.81 (t, J=7.2 Hz, 1H), 4.17 (m, 1H), 4.5-4.6 (m, 3H), 4.7-4.8 (m, 3H).

Example 7E

Removal of Acetyl Groups from 18

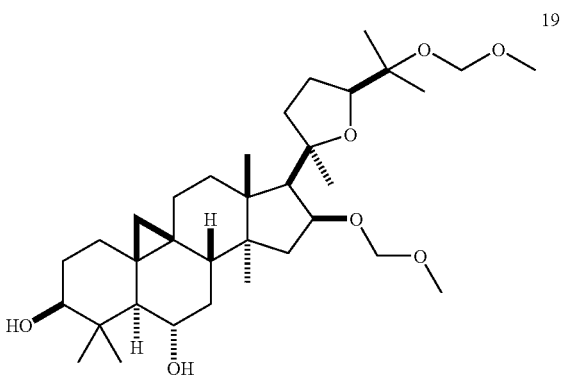

A mixture of 18, above (3,6-diacetyl-16, 25-di(methoxymethyl)ether derivative of cycloastragenol) (102 mg, 0.150 mmol) and sodium methoxide (0.5 mol/L in methanol, 10 mL) was stirred at room temperature for 48 h. Water was added, and the mixture was extracted with ethyl acetate. The organic layer was washed with water and brine and dried on anhydrous sodium sulfate. The solvent was removed under reduced pressure, and the residue was purified by silica gel column chromatography (1:1 hexane/ethyl acetate) to afford the di(methoxymethyl)ether compound 19 (80 mg, 92%).

ESI-MS m/z 579 (M+H)$^+$ C$_{34}$H$_{58}$O$_7$=578. $^1$H NMR (400 MHz, CDCl$_3$) δ (ppm) 0.32 (d, J=4.7 Hz, 1H), 0.48 (d, J=4.3 Hz, 1H), 0.89 (s, 3H), 0.93 (s, 3H), 1.1-2.0 (m, 18H), 1.15 (s, 3H), 1.17 (s, 3H), 1.22 (s, 3H), 1.29 (s, 3H), 1.34 (s, 3H), 2.29 (d, J=8.6 Hz, 1H), 3.28 (m, 1H), 3.30 (s, 3H), 3.33 (s, 3H), 3.53 (m, 1H), 3.81 (t, J=7.2 Hz, 1H), 4.18 (td, J=7.8, 5.5 Hz, 1H), 4.50 (d, J=6.6 Hz, 1H), 4.54 (d, J=6.2 Hz, 1H), 4.71 (d, J=7.0 Hz, 1H), 4.76 (d, J=7.4 Hz, 1H).

Example 8

Alkylation of Triacetyl Cycloastragenol 15, Followed by Removal of Acetyl Groups

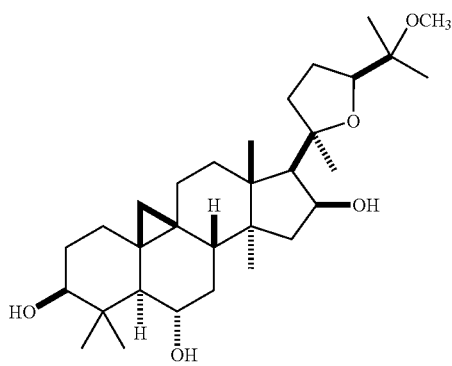

To a solution of 15 (30 mg, 0.049 mmol) in dimethylformamide (3 mL) were added iodomethane (0.75 mL, 12 mmol) and sodium hydride (60% oil dispersion, 40 mg, 1.0 mmol) at 0° C. under nitrogen, and the mixture was stirred at room temperature overnight. Water was added, and the mixture was extracted with ethyl acetate. The organic layer was washed with water and brine and dried on anhydrous sodium sulfate. The solvent was removed under reduced pressure.

To the residue was added sodium methoxide in methanol (0.5 mol/L, 6 mL), and the mixture was stirred at room temperature overnight. 10% Hydrochloric acid was added, and the mixture was extracted with ethyl acetate. The organic layer was washed with water and brine and dried on anhydrous sodium sulfate. The solvent was removed under reduced pressure, and the residue was purified by silica gel column chromatography (1:2 hexane/ethyl acetate) to afford 20 (23 mg, 93%).

ESI-MS m/z 505 $(M+H)^+$ $C_{31}H_{52}O_5=504$. $^1$H NMR (400 MHz, CDCl$_3$) δ (ppm) 0.33 (d, J=4.3 Hz, 1H), 0.48 (d, J=4.3 Hz, 1H), 0.8-2.1 (m, 17H), 0.91 (s, 3H), 0.93 (s, 3H), 1.04 (s, 3H), 1.14 (s, 3H), 1.20 (s, 3H), 1.22 (s, 3H), 1.23 (s, 3H), 2.28 (d, J=7.8 Hz, 1H), 2.60 (q, J=10.9 Hz, 1H), 3.17 (s, 3H), 3.27 (m, 1H), 3.51 (td, J=9.8, 3.5 Hz, 1H), 3.72 (dd, J=9.0, 5.5 Hz, 1H), 4.62 (m, 1H).

Example 9A

Alkylation of Free Hydroxyls of Cycloastragenol Monoglycoside 6

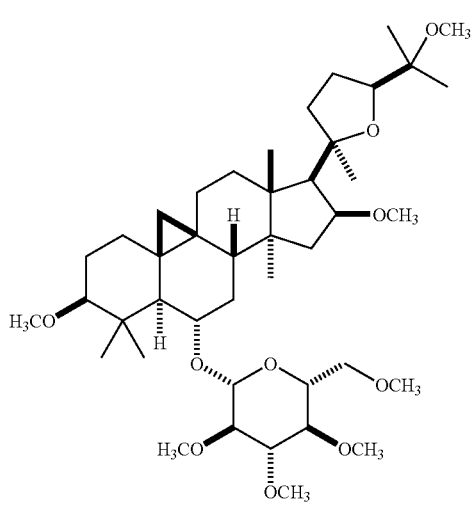

To a solution of 6 (50 mg, 0.077 mmol) in dimethylformamide (4 mL) were added iodomethane (1.0 mL, 16 mmol) and sodium hydride (60% oil dispersion, 60 mg, 1.5 mmol) at 0° C. under nitrogen, and the mixture was stirred at room temperature overnight. Water was added, and the mixture was extracted with ethyl acetate. The organic layer was washed with water and brine and dried on anhydrous sodium sulfate. The solvent was removed under reduced pressure, and the residue was purified by silica gel column chromatography (3:1 hexane/ethyl acetate) to afford permethoxy compound 21 (33 mg, 57%).

ESI-MS m/z 751 $(M+H)^+$ $C_{43}H_{74}O_{10}=750$. $^1$H NMR (400 MHz, CDCl$_3$) δ (ppm) 0.21 (d, J=4.7 Hz, 1H), 0.47 (d, J=4.3 Hz, 1H), 0.8-2.0 (m, 17H), 0.87 (s, 3H), 0.89 (s, 3H), 1.05 (s, 3H), 1.13 (s, 3R), 1.17 (s, 3H), 1.22 (s, 3H), 2.3-2.4 (m, 2H), 2.67 (dd, J 11.0, 4.1 Hz, 1H), 2.92 (t, J=8.2 Hz, 1H), 3.06 (s, 3H), 3.1-3.6 (m, 6H), 3.22 (s, 3H), 3.32 (s, 3H), 3.35 (s, 3H), 3.48 (s, 3H), 3.49 (s, 3H), 3.59 (s, 3H), 3.80 (dd, J=9.0, 6.6 Hz, 1H), 3.94 (m, 1H), 4.24 (d, J=7.4 Hz, 1H).

Example 9B

Preparation of 3,16,25-trimethoxy Astragenol, 22: Removal of Glycoside from Permethoxy Compound 21, with Concomitant Rearrangement

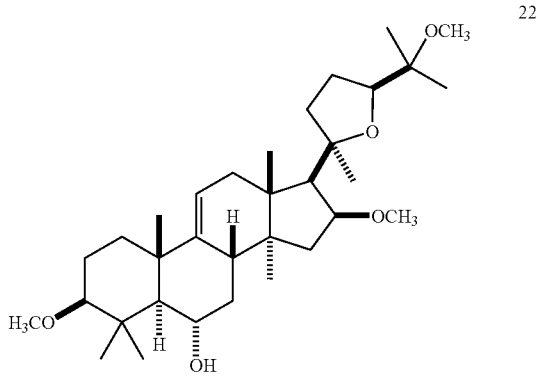

To a solution of 21 (30 mg, 0.040 mmol) in methanol (10 mL) was added sulfuric acid (0.2 mL), and the mixture was refluxed for 10 h. Water was added, and the mixture was extracted with ethyl acetate. The organic layer was washed with water and brine and dried on anhydrous sodium sulfate. The solvent was removed under reduced pressure, and the residue was purified by silica gel column chromatography (4:1 hexane/ethyl acetate) to afford 22 (3.6 mg, 17%).

ESI-MS m/z 533 $(M+H)^+$ $C_{33}H_{56}O_5=532$. $^1$H NMR (400 MHz, CDCl$_3$) δ (ppm) 0.73 (s, 3H), 0.8-2.0 (m, 18H), 0.85 (s, 3H), 1.00 (s, 3H), 1.03 (s, 3H), 1.06 (s, 3H), 1.14 (s, 3H), 1.24 (s, 3H), 1.25 (s, 3H), 2.3-2.4 (m, 2H), 2.58 (dd, J=10.9, 3.9 Hz, 1H), 3.09 (s, 3H), 3.24 (s, 3H), 3.34 (s, 3H), 3.80 (dd, J=9.4, 6.6 Hz, 1H), 3.98 (m, 1H), 5.25 (br d, J=5.5 Hz, 1H).

Example 10A

Alkylation of Free Hydroxyls of Cycloastragenol Monoglycoside 7

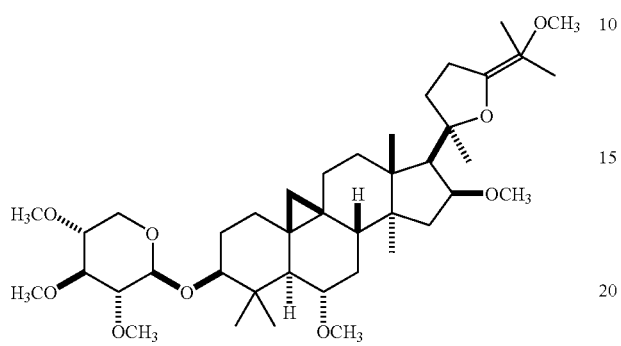

23

Compound 23 (18 mg, 53%) was obtained from 7 (30 mg) according to the procedure used for preparation of compound 21, above.

ESI-MS m/z 707 (M+H)$^+$ $C_{41}H_{70}O_9$=706. $^1$H NMR (400 MHz, CDCl$_3$) δ (ppm) 0.20 (d, J=4.3 Hz, 1H), 0.44 (d, J=4.3 Hz, 1H), 0.8-1.9 (m, 17H), 0.90 (s, 3H), 0.93 (s, 3H), 1.05 (s, 3H), 1.11 (s, 3H), 1.13 (s, 3H), 1.18 (s, 3H), 1.23 (s, 3H), 2.3-2.4 (m, 2H), 2.9-3.6 (m, 6H), 3.09 (s, 3H), 3.20 (s, 3H), 3.22 (s, 3H), 3.42 (s, 3H), 3.58 (s, 3H), 3.59 (s, 3H), 3.80 (dd, J=9.0, 6.6 Hz, 1H), 3.9-4.0 (m, 2H), 4.21 (d, J=7.4 Hz, 1H).

Example 10B

Preparation of 6,16,25-trimethoxy Astragenol, 24: Removal of Glycoside from Permethoxy Compound 23, with Concomitant Rearrangement

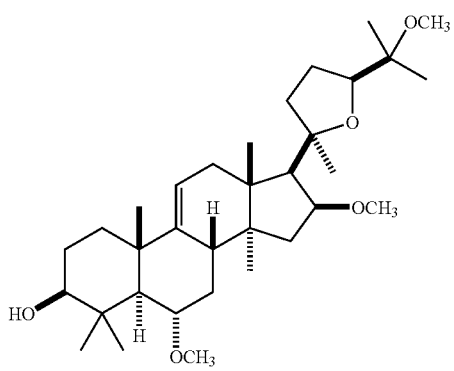

24

Compound 24 (7.1 mg, 56%) was obtained from 23 (17 mg) according to the procedure used for preparation of compound 22, above.

ESI-MS m/z 533 (N+H)$^+$ $C_{33}H_{56}O_5$=532. $^1$H NMR (400 MHz, CDCl$_3$) δ (ppm) 0.74 (s, 3H), 0.8-2.4 (m, 18H), 0.85 (s, 3H), 0.92 (s, 3H), 1.03 (s, 3H), 1.06 (s, 3H), 1.14 (s, 3H), 1.23 (s, 3H), 1.24 (s, 3H), 3.10 (s, 3H), 3.18 (m, 1H), 3.23 (s, 3H), 3.34 (s, 3H), 3.53 (m, 1H), 3.80 (dd, J=9.4, 6.6 Hz, 1H), 3.97 (m, 1H), 5.24 (d, J=5.5 Hz, 1H).

Example 11

Preparation of 3,6-dimethoxy Cycloastragenol 25: Methylation of 16,25-di(methoxymethyl)ether Compound 19, with Removal of di(methoxymethyl)ether Groups

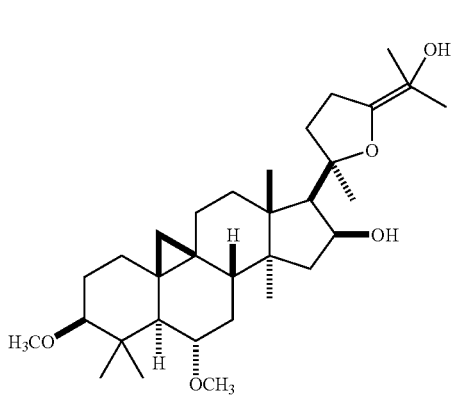

25

To a solution of 19 (30 mg, 0.052 mmol) in dimethylformamide (3 mL) were added iodomethane (0.75 mL, 12 mmol) and sodium hydride (60% oil dispersion, 40 mg, 1.0 mmol) at 0° C. under nitrogen, and the mixture was stirred at room temperature overnight. Water was added, and the mixture was extracted with ethyl acetate. The organic layer was washed with water and brine and dried on anhydrous sodium sulfate. The solvent was removed under reduced pressure.

To this residue were added tetrahydrofuran (5 mL) and 10% hydrochloric acid (1 mL), and the mixture was stirred at room temperature overnight, then refluxed for 1 h. Water was added, and the mixture was extracted with ethyl acetate. The organic layer was washed with water and brine and dried on anhydrous sodium sulfate. The solvent was removed under reduced pressure, and the residue was purified by silica gel column chromatography (3:1~1:1 hexane/ethyl acetate) to afford 25 (13 mg, 48%) and a smaller amount (7.4 mg, 25%) of the 3,6-dimethoxy-16-(methoxymethyl)ether compound 26.

25: ESI-MS m/z 563 (M+H)$^+$ $C_{34}H_{58}O_6$=562. $^1$H NMR (400 MHz, CDCl$_3$) δ (ppm) 0.19 (d, J=4.7 Hz, 1H), 0.45 (J=4.3 Hz, 1H), 0.8-2.3 (m, 18H), 0.86 (s, 3H), 0.92 (s, 3H), 1.05 (s, 3H), 1.07 (s, 3H), 1.20 (s, 3H), 1.24 (s, 3H), 1.28 (s, 3H), 2.41 (d, J=8.2 Hz, 1H), 2.70 (dd, J=11.1, 4.5 Hz, 1H), 2.90 (m, 1H), 3.19 (s, 3H), 3.326 (s, 3H), 3.330 (s, 3H), 3.71 (t, J=7.4 Hz, 1H), 4.37 (m, 1H), 4.53 (d, J=6.2 Hz, 1H), 4.59 (d, J=6.2 Hz, 1H).

26: ESI-MS m/z 519 (M+H)$^+$ $C_{32}H_{54}O_5$=518. $^1$H NMR (400 MHz, CDCl$_3$) δ (ppm) 0.21 (d, J=4.3 Hz, 1H), 0.45 (d, J=4.3 Hz, 1H), 0.8-2.0 (m, 17H), 0.86 (s, 3H), 0.93 (s, 3H), 1.06 (s, 3H), 1.12 (s, 3H), 1.20 (s, 3H), 1.21 (s, 3H), 1.28 (s, 3H), 2.30 (d, J=7.8 Hz, 1H), 2.54 (q, J=10.2 Hz, 1H), 2.69 (dd, J=11.3, 4.3 Hz, 1H), 2.89 (td, J=8.2, 4.3 Hz, 1H), 3.19 (s, 3), 3.32 (s, 3H), 3.72 (t, J=7.2 Hz, 1H), 4.66 (m, 1H).

Example 12

Exemplary Cosmetic Formulations

The following are examples of cosmetic formulations incorporating the subject compounds. An exemplary oil-in-water emulsion can be prepared using the following ingredients:

| | Ingredient | Weight % |
|---|---|---|
| PHASE A: | Water U.S.P. | (to 100) |
| | Disodium EDTA | 0.15 |
| | Glycerin | 5 |
| PHASE B: | Cetyl hydroxy ethyl cellulose | 0.15 |
| | Methyl paraben | 0.25 |
| PHASE C: | Cetyl alcohol | 0.5 |
| | Stearyl alcohol | 0.5 |
| | Behenyl alcohol | 0.5 |
| | Cetyl ricinoleate | 3 |
| | Steareth-2 (Brij 72) | 1 |
| | Distearyldimonium chloride | 0.25 |
| | Propyl Paraben | 0.1 |
| | Myristyl myristate | 1.5 |
| | Caprylic/Capritryglycerides | 1.5 |
| | Mineral oil | 2 |
| | Sugar fatty acid ester$^a$ | 1 |
| | Polypropylene glycol-15 stearyl ether | 1 |
| PHASE D: | Dimethicone 10 CST (Dow Corning) | 2 |
| PHASE E: | Compound | (to give 0.075% w/v) |
| | Isopropanol | 10 |
| | Benzyl alcohol | 10 |
| PHASE F: | 50% NaOH | (to pH 7) |

$^a$For example, a sucrose polyester having a degree of esterification of 7–8, where the fatty acids are C18 mono- and/or di-unsaturated and C22 saturated, e.g. SEFA Cottonate.

The phase A components are blended at a temperature of about 70-80° C., and the phase B components are then added at the same temperature and blended to form a uniform mixture. The phase C components are milled to obtain an acceptably smooth mixture, then added to the above mixture. The mixture is blended and allowed to cool to about 45° C., at which point dimethicone (phase D) is added, followed by the extract in a lower alcohol such as ethanol (phase E), and NaOH (phase F) to pH 7.

Further exemplary oil-in-water emulsions can be prepared from ingredients as shown in the tables below, again using conventional formulating techniques, such as follows. Distilled water (Phase A) is purged with nitrogen, followed by addition of Phase B ingredients. Phase C ingredients are then dispersed into Phase A/B until uniform, heating to about 75° C. Phase D ingredients are blended separately and heated to about 75° C., then blended into phases A/B/C under nitrogen for approx. 30 minutes, followed by addition of the combined phase E ingredients. The mixture is blended until homogeneous and then cooled. The phase F, G, and H ingredients are added, respectively, to the mixture when it has cooled to 50° C. (phase F), 40° C. (phase G) and 30° C. (phase H). Mixing is continued until the mixture is uniform.

| | Ingredient | Weight % |
|---|---|---|
| Phase B | Glycerin | 5 |
| Phase C | Glycerin | 1 |
| | EDTA | 0.1 |
| | Carbopol 954 | 0.5–0.68 |
| | Carbopol 1382 | 0.1 |
| Phase D | Cetyl alcohol | 0.72 |
| | Stearyl alcohol | 0.48 |
| | Stearic acid | 0.1 |
| | PEG-100 stearate | 0.1 |
| | Arlatone 2121 | 1 |
| | Silicone Q21403 | 2 |
| | Sugar fatty acid ester | 0.67 |
| | Tocopherol acetate | 0–0.5 |
| | Niacinamide | 2 |

| | Ingredient | Weight % |
|---|---|---|
| Phase E | Distilled water | 2 |
| | NaOH | (to pH 7) |
| Phase F | Urea | 0–2 |
| | D-Panthenol | 0–0.5 |
| | Distilled water | 5 |
| Phase G | Glydant Plus | 0.1 |
| | Glycerin | 1 |
| | Distilled water | 1 |
| Phase H | Methyl and/or isopropyl isostearate | 2.6 |
| | BHT | 0.05 |
| | Tween 20 | 0.04 |
| | Compound | (to give 0.25% w/v) |

| | Ingredient | Weight % |
|---|---|---|
| Phase B | Glycerin | 6 |
| Phase C | Glycerin | 3 |
| | Carbopol 954 | 0.4 |
| | EDTA | 0.1 |
| Phase D | Cetyl palmitate | 1.5 |
| | Cetyl alcohol | 2.25 |
| | Stearyl alcohol | 1.5 |
| | Stearic acid | 0.31 |
| | PEG-100 stearate | 0.31 |
| | Silicone wax DC2501 | 2 |
| | DC 3225C | 1.88 |
| | Dimethicone 200/350CST | 0.63 |
| | Tocopherol acetate | 0–0.5 |
| | Niacinamide | 2 |
| Phase E | Distilled water | 2 |
| | NaOH | (to pH 7) |
| Phase F | D-Panthenol | 0–0.5 |
| | Distilled water | 0–5 |
| Phase G | Glydant Plus | 0.1 |
| | Distilled water | 1 |
| | Glycerin | 1 |
| Phase H | Isopropyl palmitate | 1.25 |
| | Tween 80 | 0–0.04 |
| | BHT | 0–0.05 |
| | Compound | (to give 0.05% w/v) |

A high internal phase water-in-oil emulsion can be prepared using the following components:

| Ingredient | Weight % |
|---|---|
| Compound | (to give 0.1% w/v) |
| 1,3-dimethyl-2-imidazolidinone | 0.2 |
| Brij 92 (Polyoxyethylene (2) oleyl ether) | 5 |
| Bentone 38 (Quaternium 18-hectorite) | 0.5 |
| MgSO$_4$•7H$_2$O | 0.3 |
| Butylated hydroxy toluene | 0.01 |
| Perfume | qs |
| Water | (to 100) |

An oil-in-water cream can be prepared using the following components:

| Ingredient | Weight % |
|---|---|
| Compound | (to give 0.05% w/v) |
| Glycolic Acid | 8 |
| Mineral oil | 4 |
| 1,3-dimethyl-2-imidazolidinone | 1 |
| Brij 56 (Cetyl alcohol POE (10)) | 4 |
| Cetyl alcohol | 4 |
| Triethanolamine | 0.75 |
| Butane-1,3-diol | 3 |
| Xanthan gum | 0.3 |

-continued

| Ingredient | Weight % |
| --- | --- |
| Perfume | qs |
| Butylated hydroxy toluene | 0.01 |
| Water | (to 100) |

An alcoholic lotion can be prepared using the following components:

| Ingredient | Weight % |
| --- | --- |
| Compound | (to give 0.25% w/v) |
| 1,3-dimethyl-2-imidazolidinone | 0.1 |
| Ethanol | 40 |
| Perfume | qs |
| Butylated hydroxy toluene | 0.01 |
| Water | to 100 |

A sunscreen cream can be prepared using the following components:

| Ingredient | Weight % |
| --- | --- |
| Compound | (to give 1.0% w/v) |
| 1,3-dimethyl-2-imidazolidinone | 0.2 |
| Silicone oil 200 cts | 7.5 |
| Glyceryl monostearate | 3 |
| Cetosteryl alcohol | 1.6 |
| Polyoxyethylene-(20)-cetyl alcohol | 1.4 |
| Xanthan gum | 0.5 |
| Parsol 1789 (Butylmethoxydibenzoylmethane) | 1.5 |
| Parsol MCX (Octyl methoxycinnamate) | 7 |
| Perfume | qs |
| Color | qs |
| Water | to 100 |

A non-aqueous skin care composition can be prepared using the following components:

| Ingredient | Weight % |
| --- | --- |
| Compound | (to give 0.125% w/v) |
| 1,3-dimethyl-2-imidazolidinone | 1 |
| Silicone gum SE-30[a] | 10 |
| Silicone fluid 345[b] | 20 |
| Silicone fluid 344[c] | (to 100) |
| Squalene | 10 |
| Linoleic acid | 0.01 |
| Cholesterol | 0.03 |
| 2-hydroxy-n-octanoic acid | 0.7 |
| Vitamin E linoleate | 0.5 |
| Herbal oil | 0.5 |
| Ethanol | 2 |

[a]Dimethyl silicone polymer, MW ≥ 50,000, available from GEC
[b]Dimethyl siloxane cyclic pentamer, available from Dow Corning Corp.
[c]Dimethyl siloxane tetramer, available from Dow Corning Corp.

I claim:

1. A method for conditioning the skin in a subject in need thereof, comprising:
   applying topically to the skin a formulation comprising a compound selected from the group consisting of cycloastragenol and astragaloside IV,
   wherein the concentration of said compound in said formulation is from 0.1 to 5% (w/v);
   and
   wherein said formulation comprises at least one ingredient selected from the group consisting of an emulsifier, a surfactant, a thickener, a skin emollient, a lubricant, a preservative, and an antioxidant.

2. The method of claim 1, wherein the compound is cycloastragenol.

3. The method of claim 2, wherein said compound is astragaloside IV.

4. The method of claim 1, wherein the formulation further comprises one or more additional ingredients selected from the group consisting of an emulsifier, a thickener, and a skin emollient.

5. The method of claim 4, wherein the formulation comprises one or more ingredients selected from an emulsifier and a skin emollient.

6. The method of claim 5, wherein the formulation comprises a skin emollient.

7. The method of claim 1, wherein the biological activity of said compound is such that a composition containing the compound at a concentration of 1 ug/ml or less is effective to produce a telomerase activity at least 25% greater than observed in a vehicle control, as measured in a TRAP assay of keratinocyte or fibroblast cells.

8. The method of claim 1, wherein the biological activity of said compound is such that a composition containing the compound at a concentration of 1 ug/ml or less is effective to produce an amount of cell reconfluence in a scratch assay of keratinocytes which is at least 25% greater than that seen in untreated or other control cells.

* * * * *